(12) United States Patent
Öhrlein et al.

(10) Patent No.: US 9,630,982 B2
(45) Date of Patent: Apr. 25, 2017

(54) COLORED CHARGED SILSESQUIOXANES

(71) Applicant: BASF SE, Ludwigshafen (DE)

(72) Inventors: Reinhold Öhrlein, Rheinfelden-Herten (DE); Gabriele Baisch, Binzen (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 14/785,081

(22) PCT Filed: Apr. 16, 2014

(86) PCT No.: PCT/IB2014/060751
§ 371 (c)(1),
(2) Date: Oct. 16, 2015

(87) PCT Pub. No.: WO2014/170833
PCT Pub. Date: Oct. 23, 2014

(65) Prior Publication Data
US 2016/0075725 A1    Mar. 17, 2016

(30) Foreign Application Priority Data
Apr. 19, 2013 (EP) ..................................... 13164387

(51) Int. Cl.
C07F 7/10 (2006.01)
C07F 7/21 (2006.01)
C07F 7/08 (2006.01)
G02F 1/167 (2006.01)

(52) U.S. Cl.
CPC ............... C07F 7/21 (2013.01); C07F 7/084 (2013.01); G02F 1/167 (2013.01); G02F 2001/1678 (2013.01)

(58) Field of Classification Search
CPC ............ C08G 77/04; C07F 7/02; G02F 1/167
USPC ......................................... 556/422
See application file for complete search history.

(56) References Cited

U.S. PATENT DOCUMENTS

2012/0229884 A1  9/2012  Hayoz et al.
2014/0296518 A1  10/2014  Ohrlein et al.

FOREIGN PATENT DOCUMENTS

| JP | 2012530824 A | 12/2012 | |
|---|---|---|---|
| WO | WO-9736908 A1 | 10/1997 | |
| WO | WO-2006125836 A1 | 11/2006 | |
| WO | WO-2007048721 A1 | 5/2007 | |
| WO | WO 2007147742 A1 * | 12/2007 | ............ C07F 7/21 |
| WO | WO-2007147742 A1 | 12/2007 | |
| WO | WO-2008017593 A1 | 2/2008 | |
| WO | WO-2010149505 A2 | 12/2010 | |
| WO | WO-2011040882 A2 | 4/2011 | |
| WO | WO-2011054731 A1 | 5/2011 | |
| WO | WO-12102802 A1 | 8/2012 | |
| WO | WO-2013150444 A1 | 10/2013 | |

OTHER PUBLICATIONS

International Search Report for PCT/IB2014/060751 mailed Nov. 25, 2014.
Translation of the Notification of Reasons for Refusal, Japanese Patent Application No. 2016-508266, Dispatch Date Oct. 3, 2016.
Supplementary European Patent Office search report dated Feb. 3, 2017.

* cited by examiner

Primary Examiner — Porfirio Nazario Gonzalez
Assistant Examiner — Kofi Adzamli
(74) Attorney, Agent, or Firm — Drinker Biddle & Reath LLP

(57) ABSTRACT

The present invention provides salts of a cation and an anion, wherein the cation comprises
(i) a silsesquioxane moiety of formula

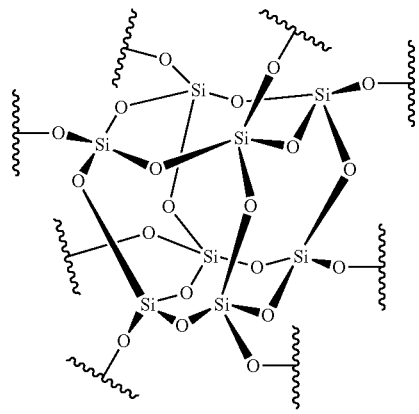

(ii) a chromophoric moiety D, which may which may be substituted with one or more substituents selected from the group consisting of $C_{1-10}$-alkyl, phenyl, halogen, $OC_{1-6}$-alkyl, OH, $NH_2$ and $NO_2$, and
(iii) a moiety of formula

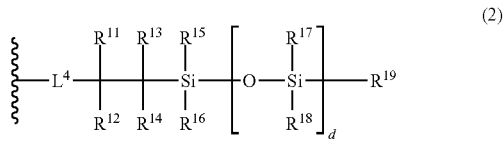

(2)

wherein
$L^4$ is $C_{1-20}$-alkylene, phenylene-$C_{1-20}$-alkylene or $C_{1-20}$-alkylene-phenylene-$C_{1-20}$alkylene,
$R^{11}$, $R^{12}$, $R^{13}$ and $R^{14}$ are independently from each other hydrogen or $C_{1-4}$-alkyl,
$R^{15}$, $R^{16}$, $R^{17}$ and $R^{18}$ are independently from each other $C_{1-4}$-alkyl,
$R^{19}$ is $C_{1-20}$-alkyl, which may be substituted with phenyl, $O-C_{1-6}$-alkyl or $NO_2$, and
d is an integer from 1 to 25,
and electrophoretic devices comprising the salts.

14 Claims, No Drawings

COLORED CHARGED SILSESQUIOXANES

CROSS-REFERENCE TO RELATED APPLICATIONS

This application is a national stage application (under 35 U.S.C. §371) of PCT/IB2014/060751, filed Apr. 16, 2014, which claims benefit of European Application No. 13164387.6, filed Apr. 19, 2013, both applications of which are incorporated herein by reference in their entirety.

The present invention refers to compounds suitable for use as charged colored particles in electrophoretic devices, and also to electrophoretic devices comprising these compounds.

BACKGROUND OF THE INVENTION

Electronic paper, also called e-paper or electronic ink, are a range of display technology, which are designed to mimic the appearance of ordinary ink on paper, but that can be written to and erased electronically. Applications of electronic paper include electronic pricing labels, time tables at bus station, mobile phone displays and e-readers able to display digital versions of books and electronic paper magazines.

Electronic paper forms visible images by rearranging charged colored particles using an applied electric field. For example, Comiskey et al. Nature 1998, 394, 253 to 255 describes a display technology called vertical electrophoretic display (EPD). In one embodiment, this technology uses microcapsules having a transparent shell and filled with numerous slightly negatively charged white titanium dioxide microparticles dispersed in a dyed (Oil Blue N) dielectric fluid. The microcapsules are dispersed in a carrier (UV curable urethane) and subsequently coated onto a transparent conductive film (indium tin oxide on polyester). Rear electrodes printed from a silver doped polymeric ink are then applied to the display layer. Applying a positive charge to one or more rear electrodes results in the migration of the slightly negatively charged white titanium dioxide microparticles to the bottom of the local microcapsule, forcing the dyed dielectric fluid to the surface and giving the pixel a black appearance. Reversing the voltage has the opposite effect.

Whereas there are currently black and white electronic papers which mimic the appearance of ordinary ink on paper sufficiently, the development of full-colour electronic papers resembling coloured ink on ordinary paper is still an area of intense research.

Full-colour electronic paper can be generated a) by modulating light in an additive system with the primaries of red, green and blue (RGB-technology), b) by using s substractive system with cyan, magenta and yellow (CMY-technology) or c) by using a substractive/additive hybrid system using both RGB and CMY primaries in a cooperative "biprimary system" (J. Heikenfeld et al. *Journal of the SID*, 2011, 19/2, 129 to 156).

Both technologies (RGB-technology or CMY technology) require a dispersion of charged coloured particles in a dielectric fluid, wherein the charged particles show a narrow size distribution and thus form homogeneous dispersions.

When using the CMY technology, for example, the charged coloured particles should have a size in the range of about 1 nm to 100 nm. When using CMY technology in video applications, it is desirable to use charged coloured particles of the the smallest particle size possible, as a decrease in particle size yields an increase in the switching frequency of the images.

WO 2007/147742 describes a coloured compound of general formula

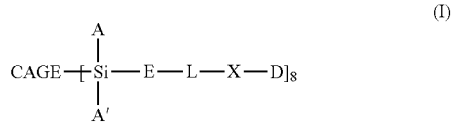

wherein
each of A and A' is, independently of the other, $C_1$-$C_4$ alkyl;
CAGE is a moiety of the formula IA

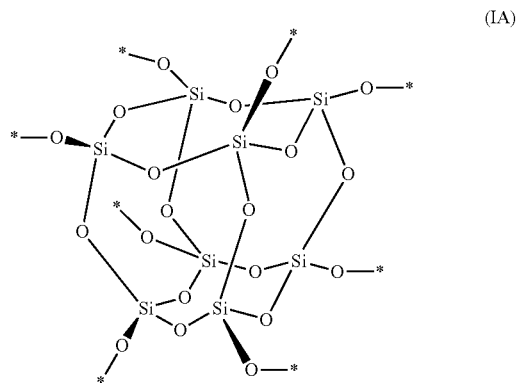 [SMILES: *O[Si]12O[Si]3(O*)O[Si]4(O*)O[Si](O*)(O1)O[Si@]1(O*)O[Si@@](O*)(O2)O[Si@@](O*)(O3)O[Si@@](O*)(O4)O1]

wherein the asterisks (*) mark the bonds binding the moieties of the formula,

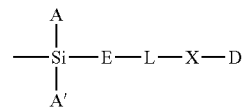

shown above, respectively,
D is a chromophoric moiety, with the proviso that all 8 moieties D in a molecule of the formula I are identical;
E is —$C(R_{3a})(R_3)$—$C(H)(R_{3b})$— and/or

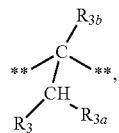

wherein the double asterisks (**) mark the binding bonds, respectively, and wherein each of $R_3$, $R_{3a}$ and $R_{3b}$, independently of the others, is hydrogen or unsubstituted or substituted $C_1$-$C_{12}$alkyl; L is unsubstituted or substituted $C_1$-$C_{25}$alkylene which is linear or branched, which alkylene may be bound* and/or be interrupted by at least one of the radicals selected from the group consisting of —O—, —S—, —N($R_4$)—, —CO—, —O—CO—, —CO—O—, —N($R_4$)—CO—, —CO—N($R_4$)— and phenylene, wherein $R_4$ is hydrogen or unsubstituted or substituted $C_1$-$C_{12}$alkyl; X is —$NR_5$— or —O—; and $R_5$ is hydrogen or unsubstituted or substituted $C_1$-$C_{12}$alkyl; or a salt thereof.

The coloured silsesquisiloxanes are used as colorants, pigments and dyes.

WO2007/048721 describes the use of functional particles as electrophoretic displaying particles, wherein the functionalized particles are $SiO_2$, $Al_2O_3$ or mixed $SiO_2$ and $Al_2O_3$ particles comprising covalently bound to an oxygen atom on the surface, a radical of formula (1),

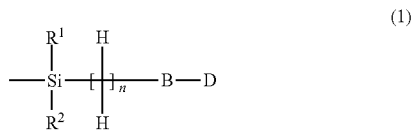

(1)

wherein $R^1$ and $R^2$ are independently of each other hydrogen, particle surface —O—, or a substituent, n is 1, 2, 3, 4, 5, 6, 7 or 8, B is the direct bond or a bridge member, and D is the residue of an organic chromophore.

WO 2010/149505 describes a composition comprising charged particles, preferably having an inorganic core of $SiO_2$, $Al_2O_3$ and/or $TiO_2$, and a counter ion comprising a silicon atom which is directly bound to a carbon atom. Said composition may be used in electrophoretic displays. Preferably, said charged particles comprise a dye attached to said inorganic core and said counter ion comprise a (poly) siloxane moiety linked via suitable bridge members to a quaternary, positively charged nitrogen or phosphorus atom, or to a moiety carrying an anionic functional group. Exemplified are charged particles having a $SiO_2$ core.

DETAILED DESCRIPTION OF THE INVENTION

The charged particles of WO 2010/149505 have several disadvantages when used in electrophoretic display applications. First, the last step of the process for the preparation of the charged particles of WO 2010/149505 has to be performed in a two phase system comprising an aqueous layer and an organic layer, for example petrol ether, and in addition produces sodium iodide as by-product. As water and sodium iodide decrease the performance of the charged particles in electrophoretic display application, water and sodium iodide have to be removed before use of the charged particles in electrophoretic display applications. In addition, the solvent of the organic layer comprising the charged particles has to be exchanged by a solvent suitable for application in electrophoretic displays such as dodecane. The removal of water and sodium iodide is tedious and usually not completely successful (traces of water and sodium iodide remain in the organic layer). The solvent exchange of the organic layer is also tedious.

Thus, it was the object of the present invention to provide charged colored particles suitable for use in full-color electronic paper.

Charged colored particles are colored particles bearing a charge or particles which are salts constituted of one or more cations and one or more anions. Ideally, the charged colored particles should show a narrow size distribution, and form homogeneous and stable dispersions or even solutions in a dielectric fluid such as dodecane. Ideally, the charged coloured particles should have a particle size suitable for use in video applications based on CMY technology, in particular a particle size in the range of 0.5 nm to 1.5 nm, preferably 0.8 to 1.2 nm.

It was also the object of the present invention to provide a process for the preparation of the charged coloured particles suitable for use in full-colour electronic paper, which process allows a convenient purification, respectively, isolation of the charged coloured particles. In particular, the process does not produce the charged coloured particles along with considerable high amounts of unwanted by-products such as water or sodium iodide, which are tedious to remove. In addition, the process allows the targeted preparation of charged particles of a well defined structure including a well-defined number of charges.

This object is solved by the compounds of claim 1, the process of claim 11, the compound of claim 12, and by the electrophoretic device of claim 14.

The present invention provides salts of a cation and an anion, wherein the cation comprises
(i) a silsesquioxane moiety of formula

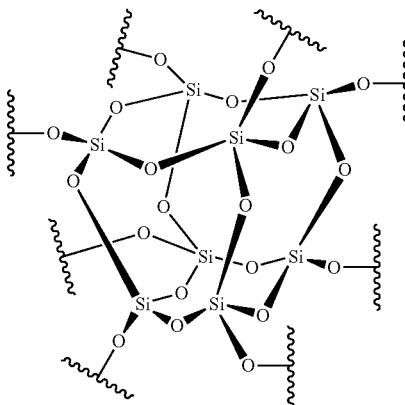

(ii) a chromophoric moiety D, which may be substituted with one or more substituents selected from the group consisting of $C_{1-10}$-alkyl, phenyl, halogen, $OC_{1-6}$-alkyl, OH, $NH_2$ and $NO_2$, and
(iii) a moiety of formula

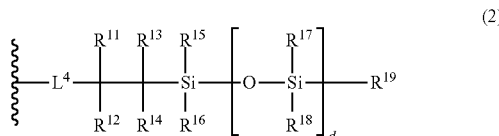

(2)

wherein
$L^4$ is $C_{1-20}$-alkylene, phenylene-$C_{120}$-alkylene or $C_{1-20}$-alkylene-phenylene-$C_{1-20}$-alkylene,
$R^{11}$, $R^{12}$, $R^{13}$ and $R^{14}$ are independently from each other hydrogen or $C_{1-4}$-alkyl,
$R^{15}$, $R^{16}$, $R^{17}$ and $R^{18}$ are independently from each other $C_{1-4}$-alkyl,
$R^{19}$ is $C_{1-20}$-alkyl, which may be substituted with phenyl, O—$C_{1-6}$-alkyl or $NO_2$, and
d is an integer from 1 to 25.

$C_{1-4}$-alkyl, $C_{1-6}$-alkyl, $C_{1-10}$-alkyl and $C_{1-20}$-alkyl can be branched or unbranched. Examples of $C_{1-4}$-alkyl are methyl ethyl, propyl, isopropyl, butyl, sec-butyl and tert-butyl. Examples of $C_{1-6}$-alkyl are $C_{1-4}$-alkyl and pentyl and hexyl.

Examples of $C_{1-10}$-alkyl are $C_{1-6}$-alkyl and heptyl, octyl, nonyl and decyl. Examples of $C_{1-20}$-alkyl are $C_{1-10}$-alkyl and undecyl, dodecyl, tridecyl, tetradecyl, pentadecyl, hexadecyl, heptadecyl, octadecyl, nonadecyl and eicosyl.

Examples of $C_{6-14}$-aryl are phenyl and naphthyl.

Examples of halogen are Cl, Br, I and F.

$C_{1-6}$-alkylene, $C_{1-10}$-alkylene and $C_{1-20}$-alkylenne can be branched or unbranched. Examples of $C_{1-6}$-alkylene are methylene, ethylene, propylene, (methyl)ethylene, butylene, pentylene and hexylene. Examples of $C_{1-10}$-alkylene are $C_{1-6}$-alkylene and heptylene, octylene, nonylene and decylene. Examples of $C_{1-20}$-alkylene are $C_{1-10}$-alkylene and undecylene, dodecylene, tridecylene, tetradecylene, pentadecylene, hexadecylene, heptadecylene, octadecylene, nonadecylene and eicosylene.

Examples of $C_{5-8}$-cydoalkylene are cydopentylene, cyclohexylene, cycloheptylene, and cyclooctylene.

Examples of $LG^1$, $LG^2$, $LG^3$ and $LG^4$ are Cl, Br and I.

Examples of $Nu^1$, $Nu^2$ and $Nu^3$ are $NH_2$ and OH.

The chromophoric moiety D can be a chromophoric moiety derived from a natural organic dye or a synthetic organic dye.

Examples of synthetic organic dyes are anthraquinone-type dyes, nitro-type dyes, acridine-type dyes, arylmethane-type dyes, azo-type dye, diazonium-type dyes, phthalocyanine-type dyes, quinine-imine dyes, thiazole-type dyes and xanthene-type dyes.

Preferably, the chromophrlc moiety D is a chromophoric moiety deriving from a synthetic organic dye, in particular from an anthraquinone-type dye or a nitro-type dye.

Examples of chromophoric moieties deriving from an anthraquinone-type dye are of formula

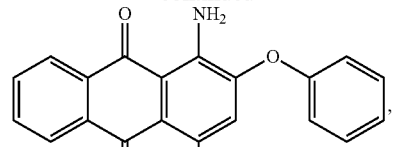,

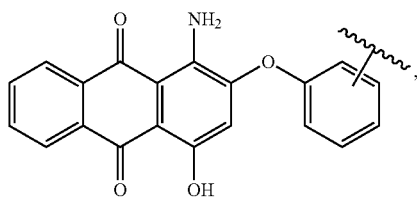

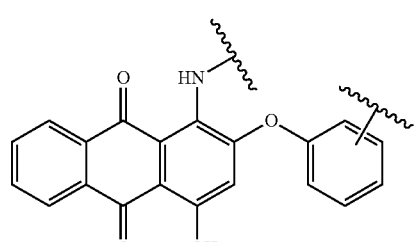

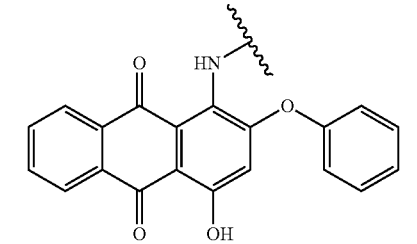

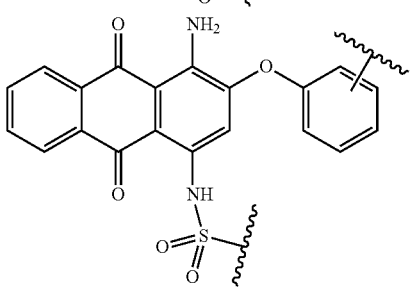

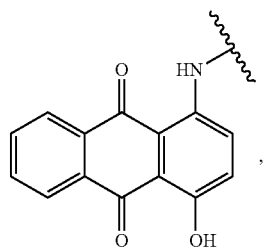,

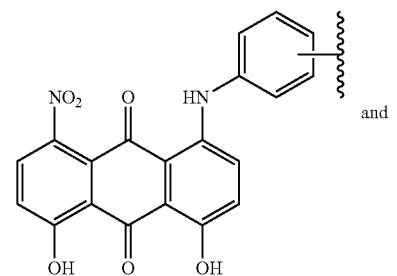

and

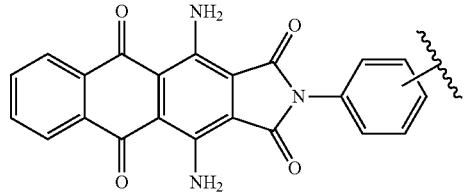

Examples of chromophoric moieties deriving from a nitro-type dye are of formula

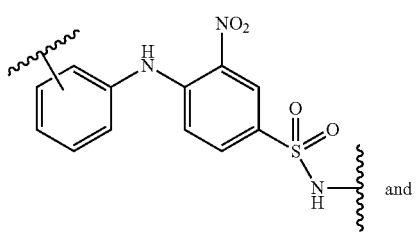

and

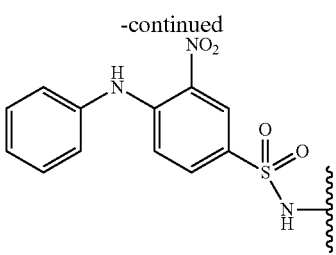

More preferably, the chromophoric moiety D is selected from the group consisting of

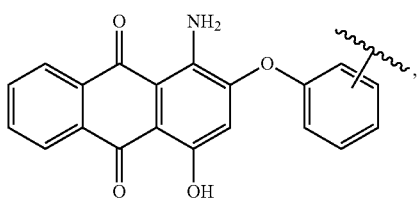

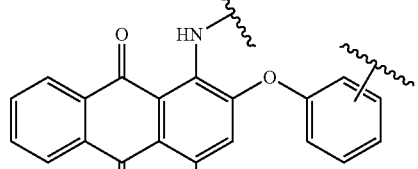

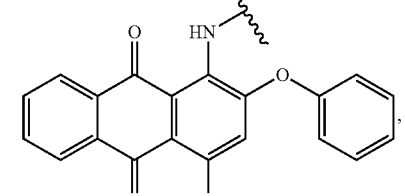

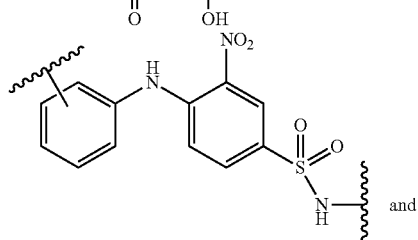 and

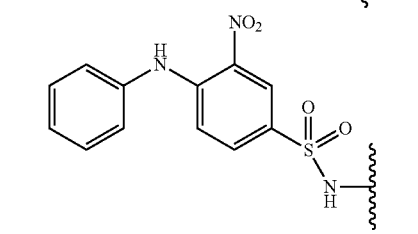

Preferred are moieties of formula (2) wherein
$L^4$ is $C_{1-20}$-alkylene, phenylene-$C_{1-20}$-alkylene or $C_{1-20}$-alkylene-phenylene-$C_{1-20}$-alkylene,
$R^{12}$ is hydrogen,
$R^{11}$, $R^{13}$ and $R^{14}$ are independently from each other hydrogen or $C_{1-4}$-alkyl,
$R^{15}$, $R^{16}$, $R^{17}$ and $R^{18}$ are independently from each other $C_{1-4}$-alkyl, $R^{19}$ is $C_{1-20}$-alkyl, which may be substituted with phenyl, O—$C_{1-6}$-alkyl or NO$_2$, and
d is an integer from 1 to 25.
More preferred are moieties of formula (2) wherein
$L^4$ is $C_{1-10}$-alkylene,
$R^{11}$, $R^{12}$, $R^{13}$ and $R^{14}$ are hydrogen,
$R^{15}$, $R^{16}$, $R^{17}$ and $R^{18}$ are methyl,
$R^{19}$ is $C_{1-10}$-alkyl, and
d is an integer from 8 to 16.
The anion may be any suitable anion. Preferably the anion is of formula

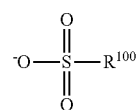

wherein
$R^{100}$ is of formula

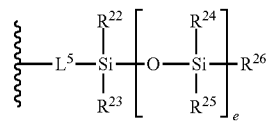

wherein
$L^5$ is $C_{1-20}$-alkylene,
$R^{22}$, $R^{23}$, $R^{24}$ and $R^{25}$ are independently from each other $C_{1-4}$-alkyl,
$R^{28}$ is $C_{1-20}$-alkyl, which may be substituted with phenyl, O—$C_{1-6}$-alkyl or NO$_2$,
e is an integer from 1 to 25, or
$R^{100}$ is —$C_{1-20}$-alkylene-Y—[—[CH$_2$]$_x$—Y—]$_y$—$C_{1-10}$-alkyl
wherein
Y is O or S,
x is an integer from 1 to 6, and
y is an integer from 1 to 25, or
$R^{100}$ is $C_{6-14}$-aryl, which may be substituted with $C_{1-20}$-alkyl, OC$_{1-6}$-alkyl or NO$_2$.
More preferably, the anion is of formula

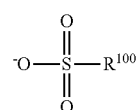

wherein
$R^{100}$ is

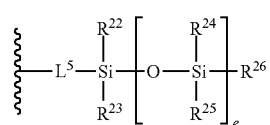

wherein
$L^5$ is $C_{1-20}$-alkylene,
$R^{22}$, $R^{23}$, $R^{24}$ and $R^{25}$ are independently from each other $C_{1-4}$-alkyl, $R^{26}$ is $C_{1-20}$-alkyl, which may be substituted with phenyl, O—$C_{1-6}$-alkyl or $NO_2$, e is an integer from 1 to 25, or $R^{100}$ is $C_{6-14}$-aryl, which may be substituted with $C_{1-20}$-alkyl, $OC_{1-6}$-alkyl or $NO_2$.

Most preferably, the anion is of formula

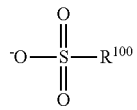

wherein $R^{100}$ is

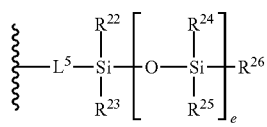

wherein $L^5$ is $C_{1-6}$-alkylene, $R^{22}$, $R^{23}$, $R^{24}$ and $R^{25}$ are independently from each other methyl, $R^{26}$ is $C_{1-10}$-alkyl, e is an integer from 8 to 16, or $R^{100}$ is phenyl, which is substituted with $C_{1-20}$-alkyl.

Preferred salts of the present invention are salts of a cation and an anion, wherein the cation comprises (i) a silsesquioxane moiety of formula

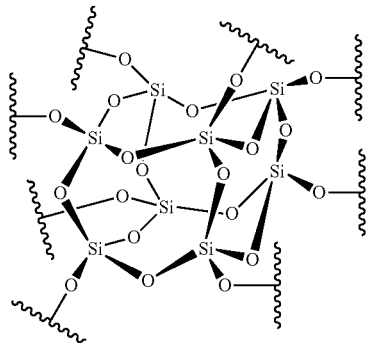

(ii) a chromophoric moiety D, which may be substituted with one or more substituents selected from the group consisting of $C_{1-10}$-alkyl, phenyl, halogen, $OC_{1-6}$-alkyl, OH, $NH_2$ and $NO_2$, and (iii) a moiety of formula

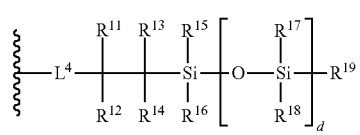

wherein $L^4$ is $C_{1-20}$-alkylene, $R^{11}$, $R^{12}$, $R^{13}$ and $R^{14}$ are independently from each other hydrogen or $C_{1-4}$-alkyl, $R^{15}$, $R^{16}$, $R^{17}$ and $R^{18}$ are independently from each other $C_{1-4}$-alkyl, $R^{19}$ is $C_{1-20}$-alkyl, which may be substituted with phenyl, O—$C_{1-6}$-alkyl or $NO_2$, d is an integer from 1 to 25, and wherein the salt is of formula

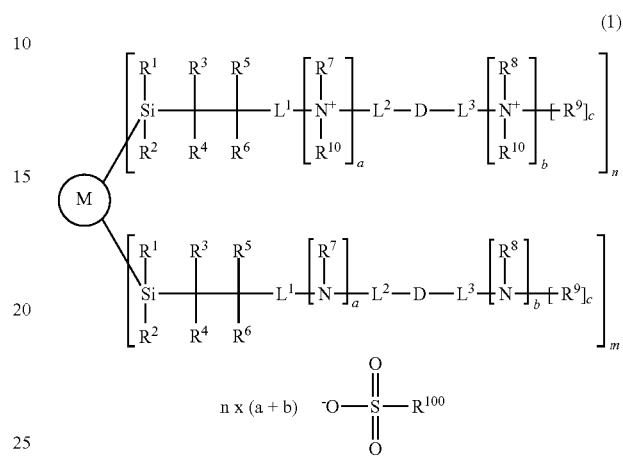

wherein

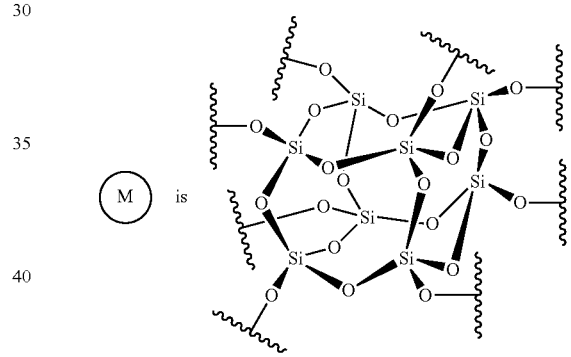

n is 1, 2, 3, 4, 5, 6, 7 or 8, m is 8-n, a is 0 or 1, b is 0 or 1, c is 0 or 1, with the proviso that at least a or b is 1, and that if b is 1, then c is also 1, $R^1$ and $R^2$ are independently from each other $C_{1-4}$-alkyl, $R^3$, $R^4$, $R^5$ and $R^6$ are independently from each other hydrogen or $C_{1-4}$-alkyl, $R^7$, $R^8$ and $R^9$ are independently from each other of formula (2) or $C_{1-20}$-alkyl, which $C_{1-20}$-alkyl may be substituted with one or more substituents selected from the group consisting of $C_{6-14}$-aryl, $OC_{1-6}$-alkyl and $NO_2$, with the proviso that at least one of $R^7$, $R^8$ and $R^9$ is of formula (2); or $R^7$ is of formula (2) and $R^8$ and $R^9$ together with the N linked to both of them form a 5, 6 or 7 membered ring, which may also Include O or S, $R^{10}$ is $C_{1-20}$-alkyl, which may be substituted with one or more substituents selected from the group consisting of $C_{6-14}$-aryl, $OC_{1-6}$-alkyl and $NO_2$, $L^1$ is -$L^{1a}$[$X^{1a}$]$_o$-[$L^{1b}$]$_r$, $L^2$ is -[$L^{2a}$]$_q$-[$X^{2a}$]$_r$-,
$L^3$ is —[$X^{3a}$]-[$L^{3a}$-$X^{3b}$]$_t$-[$L^{3b}$]$_u$-,
wherein
  o, p, q, r, s, t and u are independently from each other 0 or 1,
  $L^{1a}$, $L^{1b}$, $L^{2a}$, $L^{3a}$ and $L^{3b}$ are independently of each other $C_{1-20}$-alkylene, $C_{1-20}$-alkylene-phenylene, $C_{1-20}$-alkylene-Cc-a-cycloalkylene, phenylene or $C_{5-8}$-cycloalkylene, wherein $L^{1a}$, $L^{1b}$, $L^{2a}$, $L^{3a}$ and $L^{3b}$ may be substituted with one or more substituents selected from the group consisting of halogen, $OC_{1-6}$-alkyl, $NO_2$ and OH, or
  $L^{1b}$ and $R^7$ or $L^{2a}$ and $R^7$ together with the N linked to both of them form a 5, 6 or 7 membered ring, or
  $L^{3b}$ and $R^8$ together with the N linked to both of them form a 5, 6 or 7 membered ring, and
  $X^{1a}$, $X^{2a}$, $X^{3a}$ and $X^{3b}$ are independently of each other O, S, C(O) or C(O)O, and
D is the chromophoric moiety, which may be substituted with one or more substituents selected from the group consisting of $C_{1-10}$-alkyl, phenyl, halogen, $OC_{1-6}$-alkyl, OH, $NH_2$ and $NO_2$, and
$R^{100}$ is of formula

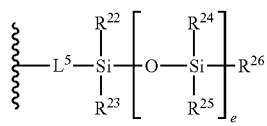

wherein
$L^5$ is $C_{1-20}$-alkylene,
$R^{22}$, $R^{23}$, $R^{24}$ and $R^{25}$ are independently from each other $C_{1-4}$-alkyl,
$R^{26}$ is $C_{1-20}$-alkyl, which may be substituted with phenyl, O—$C_{1-6}$-alkyl or $NO_2$, and
e is an integer from 1 to 25, or
$R^{100}$ is —$C_{1-20}$-alkylene-Y—[—[$CH_2$]$_x$—Y—]$_y$—$C_{1-10}$-alkyl
wherein
Y is O or S,
x is an integer from 1 to 6, and
y is an integer from 1 to 25, or
$R^{100}$ is $C_{6-14}$-aryl, which may be substituted with $C_{1-20}$-alkyl, $OC_{1-6}$-alkyl or $NO_2$.

More preferred salts of the present invention are salts of a cation and an anion, wherein the cation comprises
(i) a silsesquioxane moiety of formula

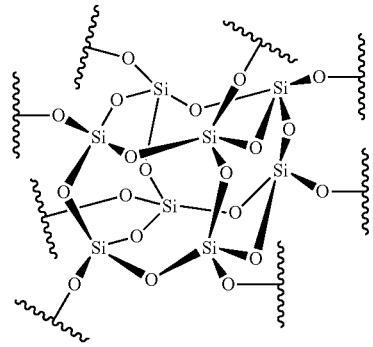

(ii) a chromophoric moiety D, which may be substituted with one or more substituents selected from the group consisting of $C_{1-10}$-alkyl, phenyl, halogen. $OC_{1-6}$-alkyl, OH, $NH_2$ and $NO_2$, and
(iii) a moiety of formula

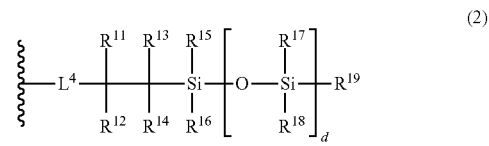

(2)

wherein
  $L^4$ is $C_{1-20}$-alkylene,
  $R^{11}$, $R^{13}$ and $R^{14}$ are independently from each other hydrogen or $C_{1-4}$-alkyl,
  $R^{12}$ is hydrogen,
  $R^{15}$, $R^{16}$, $R^{17}$ and $R^{18}$ are independently from each other $C_{1-4}$-alkyl,
  $R^{19}$ is $C_{1-20}$-alkyl, which may be substituted with phenyl, O—$C_{1-6}$-alkyl or $NO_2$, and
  d is an integer from 1 to 25, and
wherein the salt is of formula

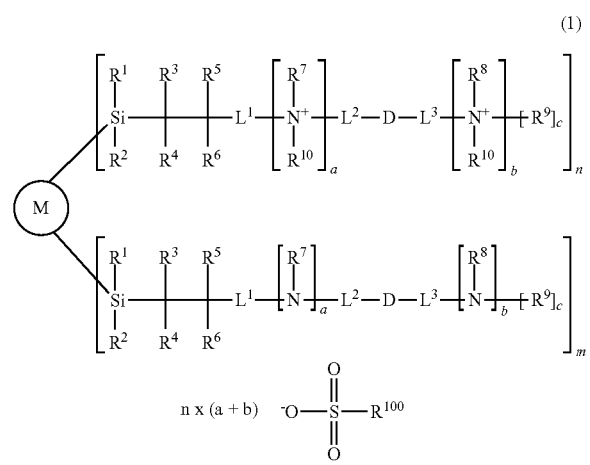

(1)

wherein

M is 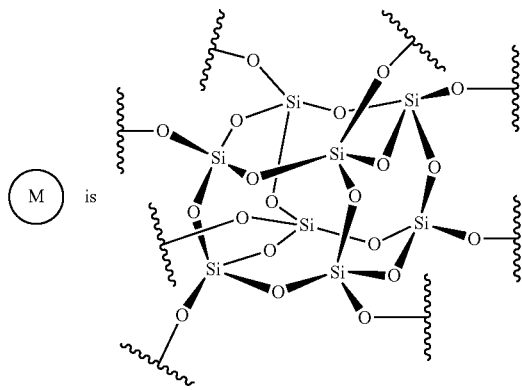

n is 1, 2, 3, 4, 5, 6, 7 or 8,
m is 8-n,
a is 0 or 1,
b is 0 or 1,
c is 0 or 1,
with the proviso that at least a or b is 1, and that if b is 1, then c is also 1,
$R^1$ and $R^2$ are independently from each other $C_{1-4}$-alkyl,
$R^3$, $R^4$ and $R^5$ are independently from each other hydrogen or $C_{1-4}$-alkyl,
$R^6$ is hydrogen
$R^7$, $R^8$ and $R^9$ are independently from each other of formula (2) or $C_{1-20}$-alkyl, which $C_{1-20}$-alkyl may be substituted with one or more substituents selected from the group consisting of $C_{6-14}$-aryl, $OC_{1-6}$-alkyl and $NO_2$, with the proviso that at least one of $R^7$, $R^8$ and $R^9$ is of formula (2),
$R^{10}$ is methyl,
$L^1$ is -L-$[X^{1a}]_o$-$[L^{1b}]_p$-,
$L^2$ is -$[L^{2a}]_q$-$[X^{2a}]_r$—,
$L^3$ is —$[X^{3a}]_s$-$[L^{3a}$-$X^{3b}]_t$-$[L^{3b}]_u$-,
wherein
    o, p, q, r, s, t and u are independently from each other 0 or 1,
    $L^{1a}$, $L^{1b}$, $L^{2a}$, $L^{3a}$ and $L^{3b}$ are independently of each other $C_{1-20}$-alkylene, $C_{1-20}$-alkylene-phenylene, $C_{1-20}$-alkylene-$C_{5-8}$-cycloalkylene, phenylene or $C_{5-8}$-cycloalkylene, wherein $L^{1a}$, $L^{1b}$, $L^{2a}$, $L^{3a}$ and $L^{3b}$ may be substituted with one or more substituents selected from the group consisting of halogen, $OC_{1-6}$-alkyl, $NO_2$ and OH, and
    $X^{1a}$, $X^{2a}$, $X^{3a}$ and $X^{3b}$ are independently of each other O, S, C(O) or C(O)O,
and
D is the chromophoric moiety, which may be substituted with one or more substituents selected from the group consisting of $C_{1-10}$-alkyl, phenyl, halogen, $OC_{1-6}$-alkyl, OH, $NH_2$ and $NO_2$, and $R^{100}$ is

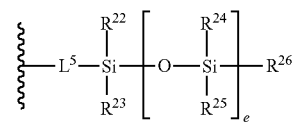

(3)

wherein
$L^5$ is $C_{1-20}$-alkylene,
$R^{22}$, $R^{23}$, $R^{24}$ and $R^{25}$ are independently from each other $C_{1-4}$-alkyl,
$R^{26}$ is $C_{1-20}$-alkyl, which may be substituted with phenyl, O—$C_{1-6}$-alkyl or $NO_2$, and
e is an integer from 1 to 25, or
$R^{100}$ is $C_{6-14}$-aryl, which may be substituted with $C_{1-20}$-alkyl, $OC_{1-6}$-alkyl or $NO_2$.

Even more preferred salts of the present invention are salts of a cation and an anion, wherein the cation comprises
    (i) a silsesquioxane moiety of formula

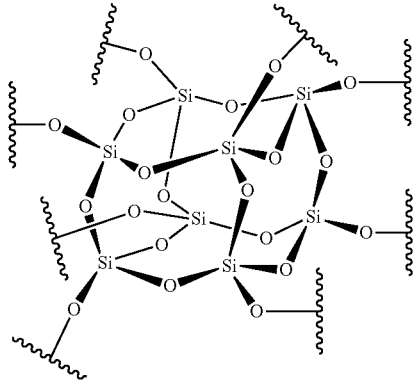 [SMILES: *O[Si]12O[Si]3(O*)O[Si@]4(O*)O[Si@](O*)(O1)O[Si@@]1(O*)O[Si@](O*)(O2)O[Si@](O*)(O3)O[Si@](O*)(O4)O1]

(ii) a chromophoric moiety D, which may be substituted with one or more substituents selected from the group consisting of $C_{1-10}$-alkyl, phenyl, halogen, $OC_{1-6}$-alkyl, OH, $NH_2$ and $NO_2$, and
    (iii) a moiety of formula

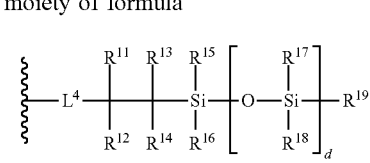

(2)

wherein
$L^4$ is $C_{1-10}$-alkylene,
$R^{11}$, $R^{12}$, $R^{13}$ and $R^{14}$ are hydrogen,
$R^{15}$, $R^{16}$, $R^{17}$ and $R^{18}$ are methyl,
$R^{19}$ is $C_{1-10}$-alkyl, and
d is an integer from 8 to 16, and
wherein the salt is of formula

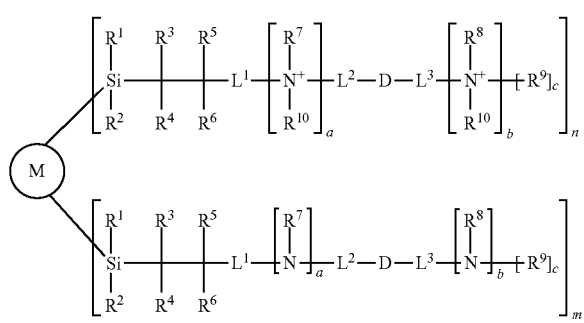

(1)

-continued

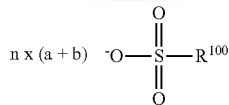

wherein

M is 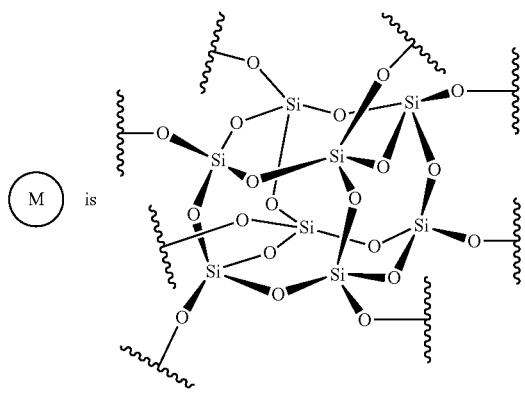

n is 1, 2, 3, 4, 5, 6, 7 or 8,
m is 8-n,
a is 0 or 1,
b is 0 or 1,
c is 0 or 1,
with the proviso that at least a or b is 1, and that if b is 1, then c is also 1,
$R^1$ and $R^2$ are methyl,
$R^3$, $R^4$, $R^5$ and $R^6$ are hydrogen,
$R^7$, $R^8$ and $R^9$ are independently from each other of formula (2) or $C_{1-6}$-alkyl, with the proviso that at least one of $R^7$, $R^8$ and $R^9$ is of formula (2),
$R^{10}$ is methyl,
$L^1$ is -$L^{1a}$-[$X^{1a}$]$_o$-[$L^{1b}$]$_p$-,
$L^2$ is -[$L^{2a}$]$_q$-[$X^{2a}$]$_r$—,
$L^3$ is —[$X^{3a}$]$_s$-[$L^{3a}$-$X^{3b}$]$_t$-[$L^{3b}$]$_u$-,
wherein
 q and u are independently from each other 0 or 1,
 o, p, r, s and t are 0,
 $L^{1a}$, $L^{1b}$, $L^{2a}$, $L^{3a}$ and $L^{3b}$ are independently of each other $C_{1-20}$-alkylene, and
 $X^{1a}$, $X^{2a}$, $X^{3a}$ and $X^{3b}$ are independently of each other O, S, C(O) or C(O)O,
and
D is the chromophoric moiety, which may be substituted with one or more substituents selected from the group consisting of $C_{1-10}$-alkyl, phenyl, halogen, $OC_{1-6}$-alkyl, OH, $NH_2$ and $NO_2$, and
$R^{100}$ is

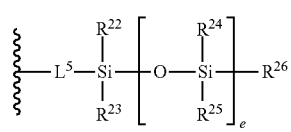   (3)

wherein
 $L^5$ is $C_{1-6}$-alkylene,
 $R^{22}$, $R^{23}$, $R^{24}$ and $R^{25}$ are independently from each other methyl,
 $R^{26}$ is $C_{1-10}$-alkyl,
 e is an integer from 8 to 16, or
 $R^{100}$ is phenyl, which is substituted with $C_{1-20}$-alkyl.

Most preferred salts of the present invention are salts of a cation and an anion, wherein the cation comprises (i) a silsesquioxane moiety of formula

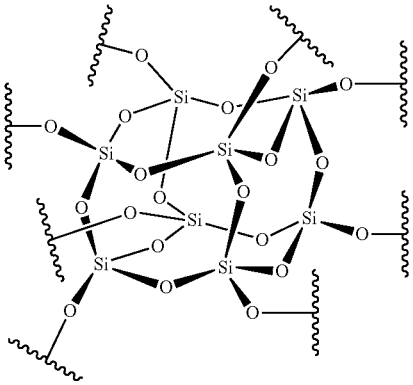 [SMILES: *O[Si]12O[Si]3(O*)O[Si@]4(O*)O[Si@](O*)(O1)O[Si@@]1(O*)O[Si@](O*)(O2)O[Si@](O*)(O3)O[Si@](O*)(O4)O1]

(ii) a chromophoric moiety D, which may be substituted with one or more substituents selected from the group consisting of $C_{1-10}$-alkyl, phenyl, halogen, $OC_{1-6}$-alkyl, OH, $NH_2$ and $NO_2$ and (iii) a moiety of formula

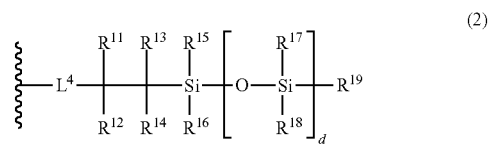   (2)

wherein
 $L^4$ is $C_{1-10}$-alkylene,
 $R^{11}$, $R^{12}$, $R^{13}$ and $R^{14}$ are hydrogen,
 $R^{15}$, $R^{16}$, $R^{17}$ and $R^{18}$ are methyl,
 $R^{19}$ is $C_{1-10}$-alkyl, and
 d is an integer from 8 to 16,
and
wherein the salt is of formula

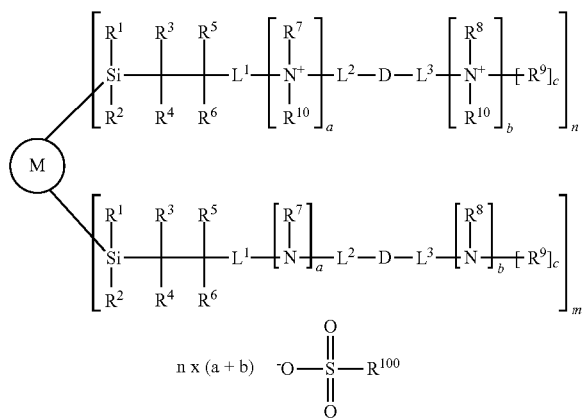

(1)

wherein

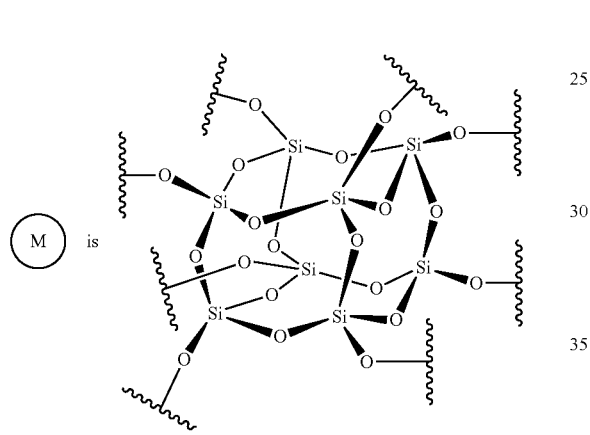

n is 1, 2, 3, 4, 5, 6, 7 or 8,
m is 8-n,
a is 0 or 1,
b is 0 or 1,
c is 0 or 1,
with the proviso that at least a or b is 1, and that if b is 1, then c is also 1,
$R^1$ and $R^2$ are methyl
$R^3$, $R^4$, $R^5$ and $R^6$ are hydrogen,
$R^7$, $R^8$ and $R^9$ are independently from each other of formula (2) or $C_{1-6}$-alkyl, with the proviso that at least one of $R^7$, $R^8$ and $R^9$ is of formula (2),
$R^{10}$ is methyl,
$L^1$ is $-L^{1a}-[X^{1a}]_o-[L^{1b}]_p-$,
$L^2$ is $-[L^{2a}]_q-[X^{2a}]_r-$,
$L^3$ is $-[X^{3a}]_s-[L^{3a}-X^{3b}]_t-[L^{3b}]_u-$,
wherein
  q and u are independently from each other 0 or 1,
  o, p, r, s and t are 0,
  $L^{1a}, L^{1b}, L^{2a}, L^{3a}$ and $L^{3b}$ are independently of each other $C_{1-20}$-alkylene, and
  $X^{1a}, X^{2a}, X^{3a}$ and $X^{3b}$ are independently of each other O, S, C(O) or C(O)O,
and
the chromophoric moiety D is selected from the group consisting of

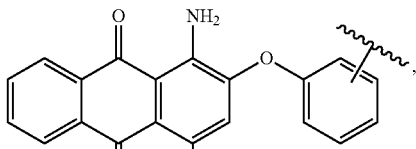

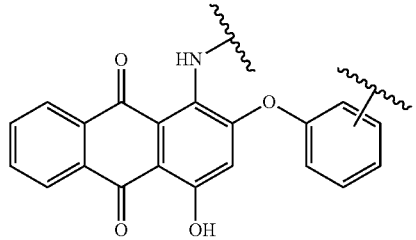

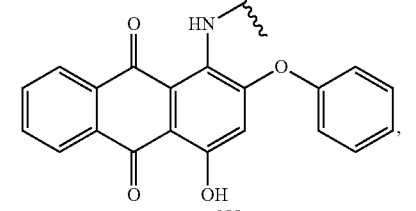

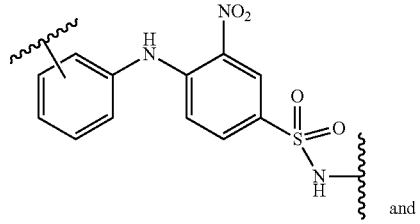
and

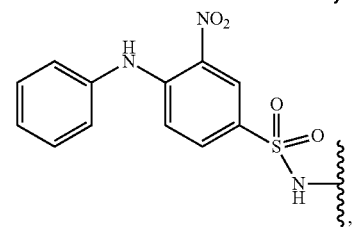
and $R^{100}$ is
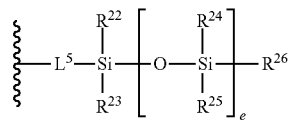
wherein
 $L^5$ is $C_{1-6}$-alkylene,
 $R^{22}$, $R^{23}$, $R^{24}$ and $R^{25}$ are methyl,
 $R^{26}$ is $C_{1-10}$-alkyl,
 e is an integer from 8 to 16, or
$R^{100}$ is phenyl, which is substituted with $C_{1-20}$-alkyl,
In particular preferred salts of the present invention are the salts of formulae
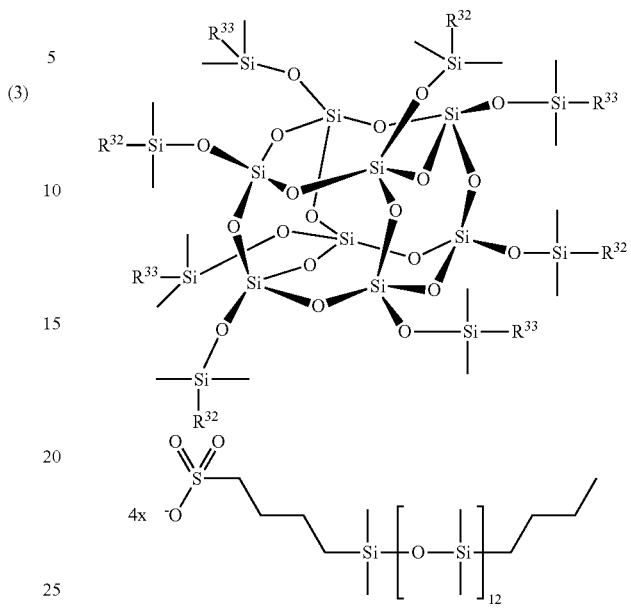
wherein
$R^{32}$ is
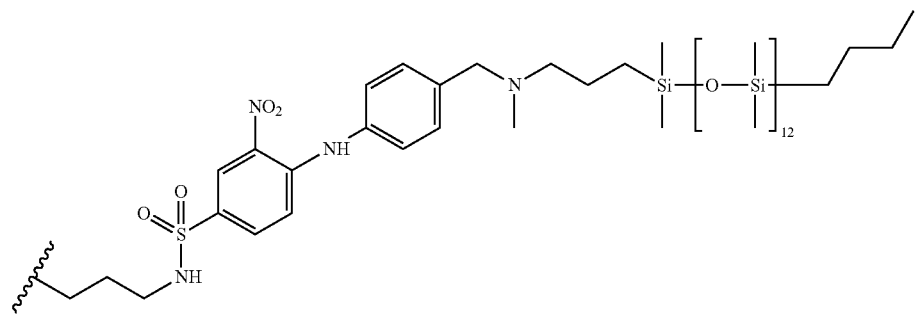
and
$R^{33}$ is
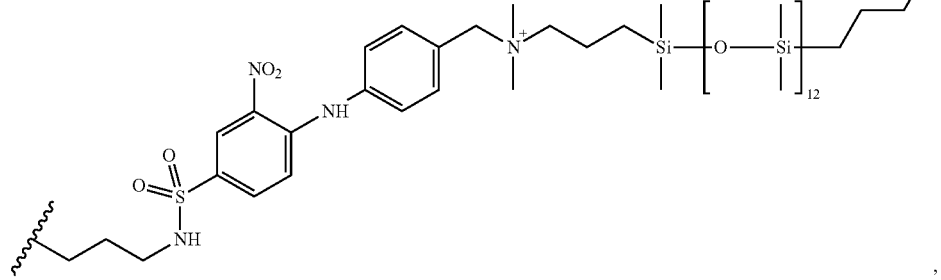

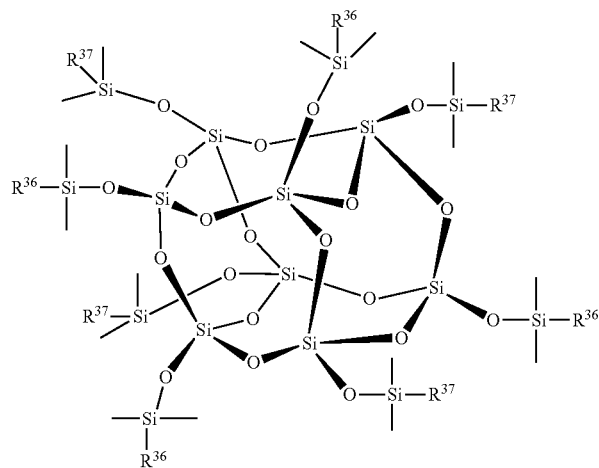
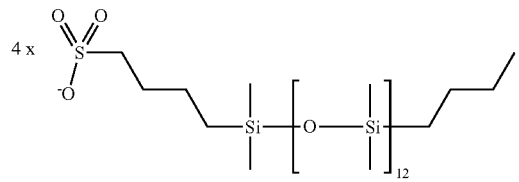
wherein
$R^{36}$ is
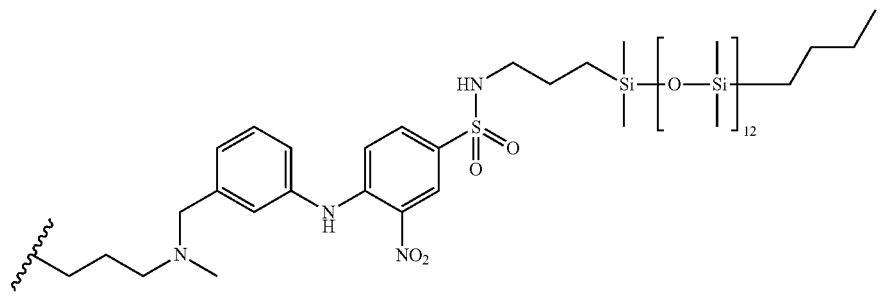
and
$R^{37}$ is
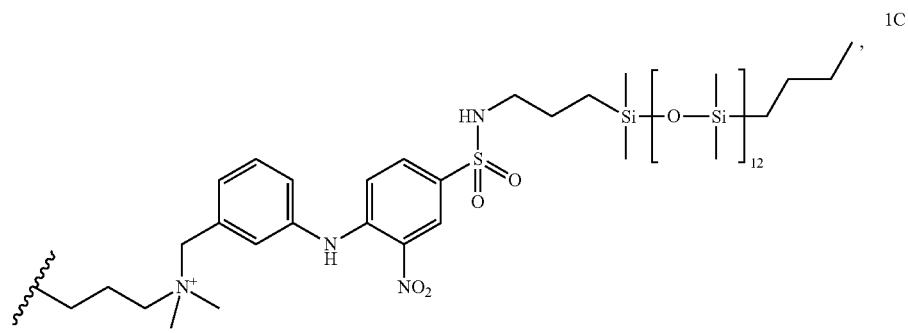

-continued
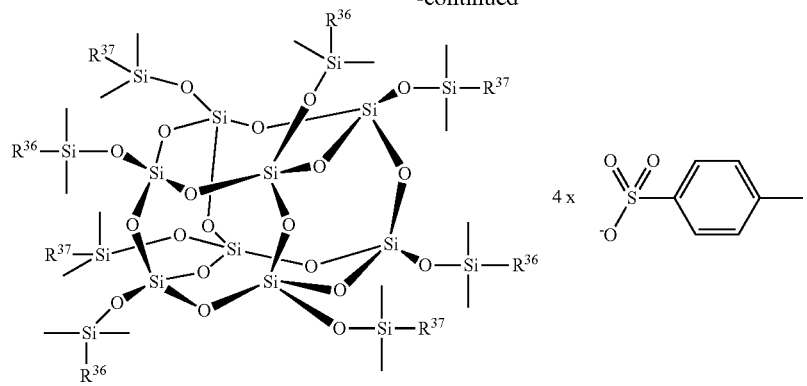
wherein
R³⁶ is
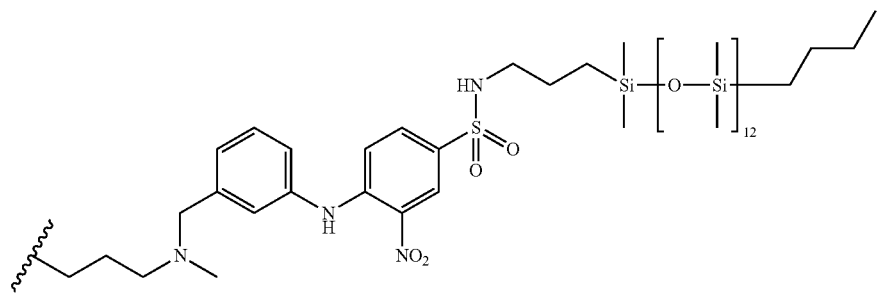
and
R³⁷ is
ID
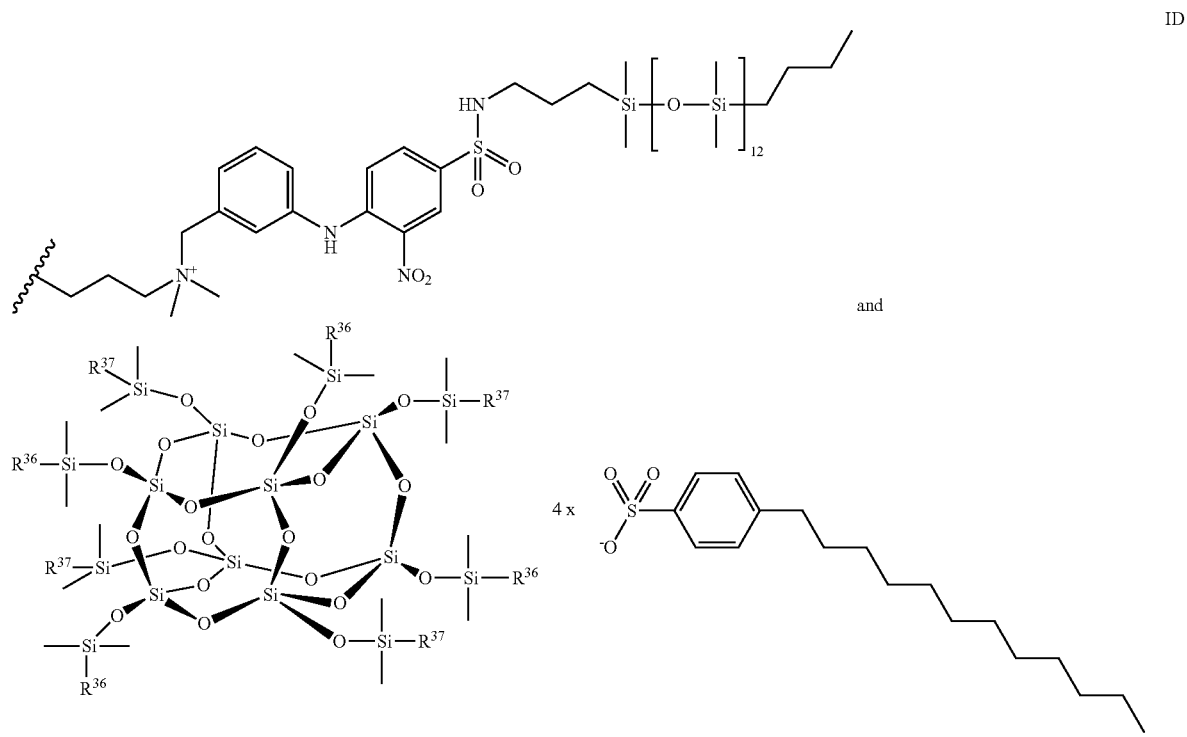
wherein
R³⁶ is

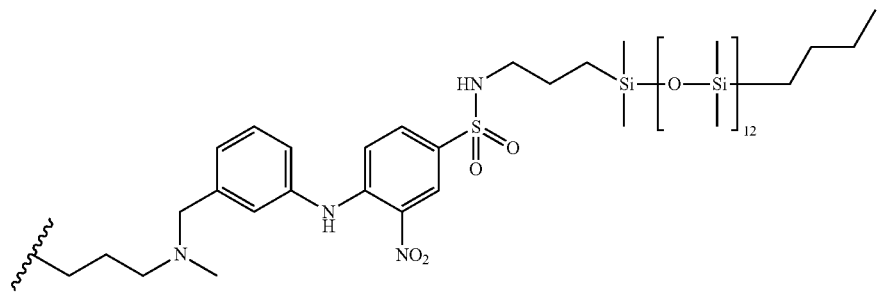

and
R³⁷ is

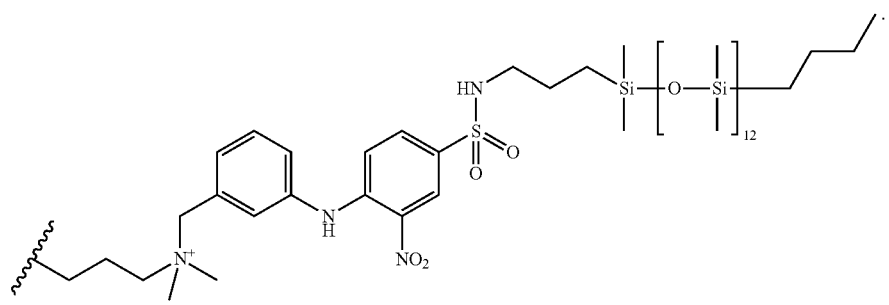

Also part of the present invention is a process for the preparation of the salts of the present invention.

The process for the preparation of the salts of formula (1)

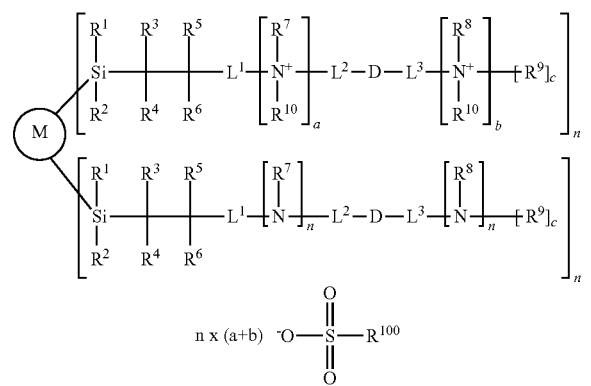

wherein

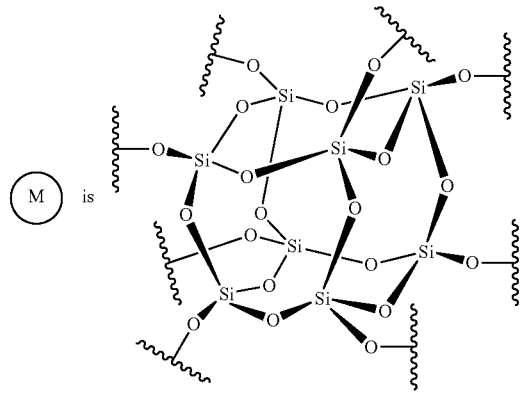 M is 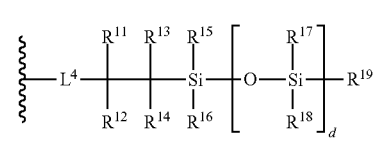

n is 1, 2, 3, 4, 5, 6, 7 or 8,
m is 8-n,
a is 0 or 1,
b is 0 or 1,
c is 0 or 1,
with the proviso that at least a or b is 1, and that if b is 1, then c is also 1,
$R^1$ and $R^2$ are independently from each other $C_{1-4}$-alkyl,
$R^3$, $R^4$, $R^5$ and $R^6$ are independently from each other hydrogen or $C_{1-4}$-alkyl,
$R^7$, $R^8$ and $R^9$ are of formula (2)

wherein
$L^4$ is $C_{1-20}$-alkylene,
$R^{11}$, $R^{12}$, $R^{13}$ and $R^{14}$ are independently from each other hydrogen or $C_{1-4}$-alkyl,
$R^{15}$, $R^{16}$, $R^{17}$ and $R^{18}$ are independently from each other $C_{1-4}$-alkyl,
$R^{19}$ is $C_{1-20}$-alkyl, which may be substituted with phenyl, O—$C_{1-6}$-alkyl or $NO_2$,
d is an integer from 1 to 25, or
$R^7$, $R^8$ and $R^9$ are independently from each other $C_{1-20}$-alkyl, which may be substituted with one or more substituents selected from the group consisting of $C_{6-14}$-aryl, $OC_{1-6}$-alkyl and $NO_2$, with the proviso that at least one of $R^7$, $R^8$ and $R^9$ is of formula (2), or
$R^7$ is of formula (2) and $R^8$ and $R^9$ together with the N linked to both of them form a 5, 6 or 7 membered ring, which may also include O or S, $R^{10}$ is $C_{1-20}$-alkyl, which may be substituted with one or more substituents selected from the group consisting of $C_{6-14}$-aryl, $OC_{1-6}$-alkyl and $NO_2$, $L^1$ is $-L^{1a}-[X^{1a}]_o[L^{1b}]_p-$,
$L^2$ is $-[L^{2a}]_q-[X^{2a}]_r-$,
$L^3$ is $-[X^{3a}]_s-[L^{3a}-X^{3b}]_t-[L^{3b}]_u-$,
wherein
  o, p, q, r, s, t and u are independently from each other 0 or 1,
  $L^{1a}$, $L^{1b}$, $L^{2a}$, $L^{3a}$ and $L^{3b}$ are independently of each other $C_{1-20}$-alkylene, $C_{1-20}$-alkylene-phenylene, $C_{1-20}$-alkylene-$C_{5-8}$-cycloalkylene, phenylene or $C_{5-8}$-cycloalkylene, wherein $L^{1a}$,
  $L^{1b}$, $L^{2a}$, $L^{3a}$ and $L^{3b}$ may be substituted with one or more substituents selected from the group consisting of halogen, $OC_{1-6}$-alkyl, $NO_2$ and OH, or
  $L^{1b}$ and $R^7$ or $L^{2a}$ and $R^7$ together with the N linked to both of them form a 5, 6 or 7 membered ring, or
  $L^{3b}$ and $R^8$ together with the N linked to both of them form a 5, 6 or 7 membered ring, and
  $X^{1a}$, $X^{2a}$, $X^{3a}$ and $X^{3b}$ are independently of each other O, S, C(O) or C(O)O,
and
D is the chromophoric moiety, which may be substituted with one or more substituents selected from the group consisting of $C_{1-10}$-alkyl, phenyl, halogen, $OC_{1-6}$-alkyl, OH, $NH_2$ and $NO_2$, and
$R^{100}$ is of formula

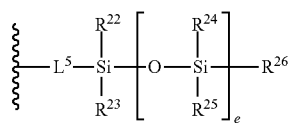

wherein
  $L^5$ is $C_{1-20}$-alkylene,
  $R^{22}$, $R^{23}$, $R^{24}$ and $R^{25}$ are independently from each other $C_{1-4}$-alkyl,
  $R^{26}$ is $C_{1-20}$-alkyl, which may be substituted with phenyl, $O-C_{1-6}$-alkyl or $NO_2$,
  e is an integer from 1 to 25, or
$R^{400}$ is $-C_{1-20}$-alkylene-Y-$[-[CH_2]_x-Y-]_y-C_{1-10}$-alkyl
wherein
  Y is O or S,
  x is an integer from 1 to 6, and
  y is an integer from 1 to 25, or
$R^{100}$ is $C_{6-14}$-aryl, which may be substituted with $C_{1-20}$-alkyl, $OC_{1-6}$-alkyl or $NO_2$,
comprises the step of reacting a compound of formula

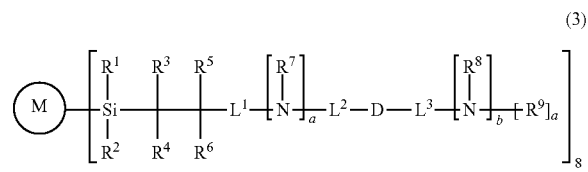

wherein
M, a, b, c, $R^1$, $R^2$, $R^3$, $R^4$, $R^5$, $R^6$, $R^7$, $R^8$, $R^9$, $L^1$, $L^2$, $L^3$ and D are as depicted in formula (1) with a compound of formula

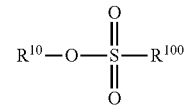

wherein
  $R^{10}$ and $R^{100}$ are as depicted for formula (1).

In a preferred process, $R^6$ and $R^{12}$ are hydrogen, and $R^{10}$ is methyl.

Preferably, the reaction is performed in an inert organic solvent such as chloroform. The reaction may be performed at elevated temperature such as 40 to 150° C., preferably at 40 to 80° C.

Depending on the mole equivalents of the compound of formula (4) used in the reaction, salts of formula (1) are obtained, wherein n is 1, 2, 3, 4, 5, 6, 7 or 8.

There are several possibilities to obtain a compound of formula (3).

For example, a compound of formula (3), wherein c is 1, $R^9$ is of formula (2) and $R^{12}$ is hydrogen may be obtained by reacting a compound of formula

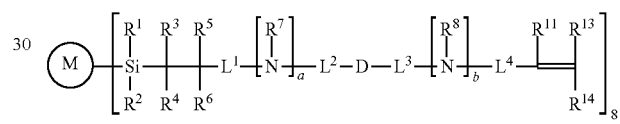

wherein
M, a, b, $R^1$, $R^2$, $R^3$, $R^4$, $R^5$, $R^6$, $R^7$, $R^8$, $R^{11}$, $R^{13}$, $R^{14}$, $L^1$, $L^2$, $L^3$, $L^4$ and D are as depicted for formula (1), with a compound of formula

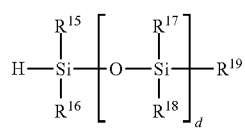

wherein
$R^{15}$, $R^{16}$, $R^{17}$, $R^{18}$, $R^{19}$ and d are as depicted for formula (1).

Preferably, the reaction is performed in the presence of a catalyst. Suitable catalysts are for example platinum containing compounds such as hexachloroplatinic acid, also known as Speier's catalyst, or $Pt_2[(CH_2=CH_2Si(Me)_2)_2O]_3$, also known as Karstedt's catalyst.

The reaction is usually performed in an inert organic solvent such as dichloromethane. The reaction is usually performed at a temperature of 25 to 80° C., preferably at a temperature of 35 to 50° C.

The reaction is usually performed in the presence of diethyl sulfide.

The compound of formula (6) is commercially available.

There are several possibilities to prepare a compound of formula (5),

For example, a compound of formula (5) may be obtained by reacting a compound of formula

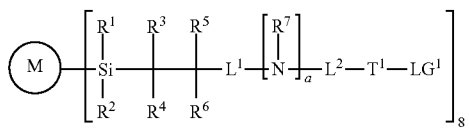
(7)

wherein
M, a, $R^1$, $R^2$, $R^3$, $R^4$, $R^5$, $R^6$, $R^7$, $L^1$ and $L^2$ are as depicted for formula (1),
$T^1$ is a part of the chromophoric moiety D, and
$LG^1$ is a leaving group,
with a compound of formula

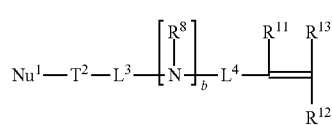
(9)

wherein
b, $R^8$, $R^{11}$, $R^{13}$, $R^{14}$, $L^3$ and $L^4$ are as depicted for formula (1),
$T^2$ is a part of the chromophoric moiety D, and
$Nu^1$ is a nucleophilic group.

The reaction is usually performed in an inert organic solvent such as dimethyl sulfoxide. The reaction is usually performed at elevated temperatures such as at temperatures from 50 to 200° C., preferably at temperatures from 80 to 120° C.

The compound of formula (7), wherein $R^6$ is hydrogen, may be obtained by reacting a compound of formula

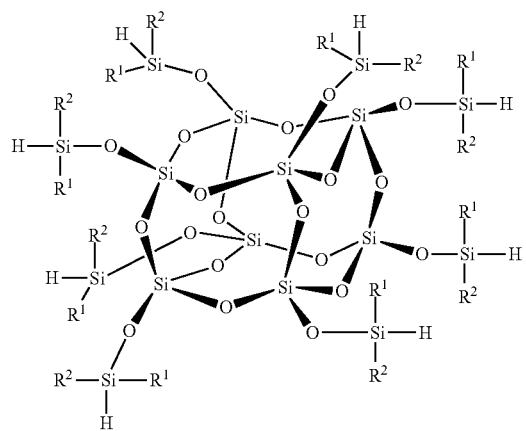
10 wherein $R^1$ and $R^2$ are as depicted in formula (1)
with a compound of formula

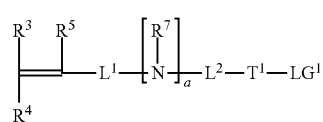
(11)

wherein
a, $R^3$, $R^4$, $R^5$, $R^7$, $L^1$ and $L^2$ are as depicted for formula (1),
$T^1$ is a part of the chromophoric moiety D, and
$LG^1$ is a leaving group.

Preferably, the reaction is performed in the presence of a catalyst. Suitable catalysts are for example platinum containing compounds such as hexachloroplatinic acid, also known as Speier's catalyst, or $Pt_2[(CH_2=CH_2Si(Me)_2)_2O]_3$, also known as Karstedt's catalyst.

The reaction is usually performed in an inert organic solvent such as dichloromethane. The reaction is usually performed at a temperature of 25 to 80° C., preferably at a temperature of 35 to 50° C.

The reaction is usually performed in the presence of diethyl sulfide.

The compound of formula (10), wherein $R^1$ and $R^2$ are methyl is commercially available. The compound of formula (10), wherein $R^1$ and $R^1$ are methyl, may also be prepared according to D. Höbbel et al., Z. Chem. 1989, 29(7), 260-261 or according to reference example C) of WO 2007/147742.

For example, a compound of formula (5) may also be obtained by reacting a compound of formula

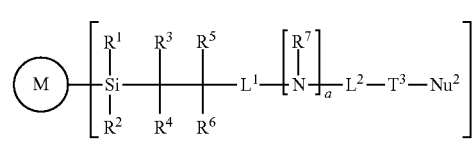
(8)

wherein
M, a, $R^1$, $R^2$, $R^3$, $R^4$, $R^5$, $R^6$, $R^7$, $L^1$ and $L^2$ are as depicted for formula (1),
$T^3$ is a part of the chromophoric moiety D, and
$Nu^2$ is a nucluophilic group,
with a compound of formula

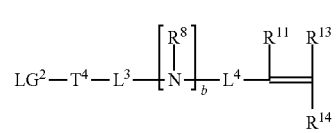
(11)

wherein
b, $R^8$, $R^{11}$, $R^{13}$, $R^{14}$, $L^3$ and $L^4$ are as depicted for formula (1),
$T^4$ is a part of the chromophoric moiety D, and
$LG^2$ is a leaving group.

The reaction is usually performed in an inert organic solvent such as dimethyl sulfoxide. The reaction is usually performed at elevated temperatures such as at temperatures from 50 to 200 C, preferably at temperatures from 80 to 120° C.

The compound of formula (8), wherein $R^6$ is hydrogen, may be obtained by reacting a compound of formula

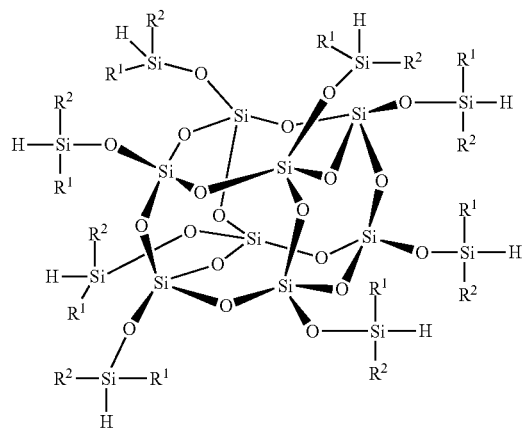

wherein $R^1$ and $R^2$ are as depicted in formula (1) with a compound of formula

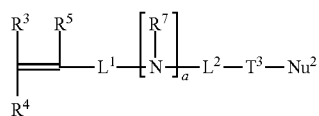
(9)

wherein
a, $R^3$, $R^4$, $R^5$, $R^7$, $L^1$ and $L^2$ are as depicted for formula (1),
$T^3$ is a part of the chromophoric moiety D, and
$Nu^2$ is a nucleophilic group.

Preferably, the reaction is performed in the presence of a catalyst. Suitable catalysts are for example platinum containing compounds such as hexachloroplatinic acid, also known as Speier's catalyst, or $Pt_2[(CH_2=CH_2Si(Me)_2)_2O]_3$, also known as Karstedt's catalyst.

The reaction is usually performed in an inert organic solvent such as dichloromethane. The reaction is usually performed at a temperature of 25 to 80° C., preferably at a temperature of 35 to 50° C.

The reaction is usually performed in the presence of diethyl sulfide.

The compound of formula (3), wherein $R^6$ is hydrogen, may also be prepared by reacting a compound of formula

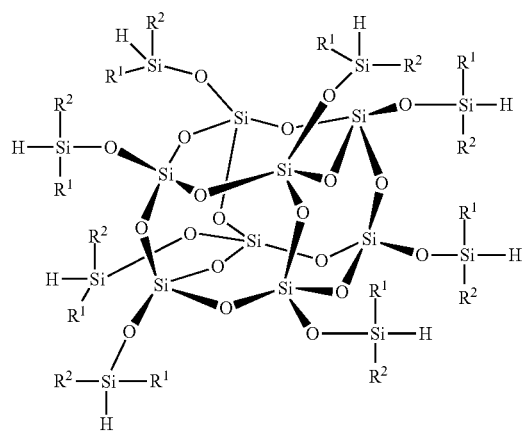

wherein $R^1$ and $R^2$ are as depicted in formula (1) with a compound of formula

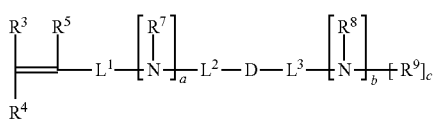
(16)

wherein
a, b, c, $R^3$, $R^4$, $R^5$, $R^7$, $R^8$, $R^9$, $L^1$, $L^2$, $L^3$ and D are as depicted for formula (1).

Preferably, the reaction is performed in the presence of a catalyst. Suitable catalysts are for example platinum containing compounds such as hexachloroplatinic acid, also known as Speier's catalyst, or $Pt_2[(CH_2=CH_2Si(Me)_2)_2O]_3$, also known as Karstedt's catalyst.

The reaction is usually performed in an inert organic solvent such as toluene. The reaction is usually performed at a temperature of 25 to 80° C., preferably at a temperature of 35 to 50° C.

The compound of formula (16) may be prepared by reacting a compound of formula

(14)

wherein
a, $R^3$, $R^4$, $R^5$, $R^7$, $L^1$ and $L^2$ are as depicted for formula (1),
$T^5$ is part of the chromophoric moiety D
$Nu^3$ is a nucleophilic group,
with a compound of formula

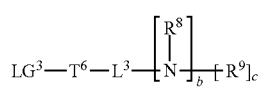
(15)

wherein
c, $R^8$, $R^9$ and $L^3$ are as depicted for formula (1),
$T^6$ is part of the chromophoric moiety D
$LG^3$ is a leaving group.

Preferably, the reaction is performed in the presence of a base, for example cesium carbonate.

The reaction is usually performed in an inert organic solvent such as chloroform. The reaction is usually performed at ambient temperature preferably at a temperature of 15 to 30° C.

The compound of formula (14) may be prepared by reacting a compound of formula

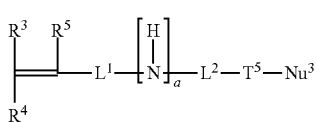
(13)

wherein a, $R^3$, $R^4$, $R^5$, $L^1$ and $L^2$ are as depicted for formula (1), $T^5$ is part of the chromophoric moiety D, $Nu^3$ is a nucleophilic group, with a compound of formula $R^7$-$LG^4$ (13), wherein $R^7$ is a depicted for formula (1), and $LG^4$ is a leaving group.

Also part of the invention is a compound of formula

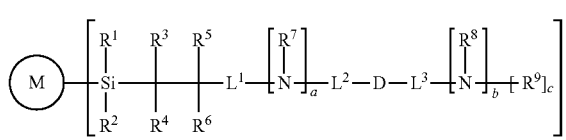
(3)

wherein

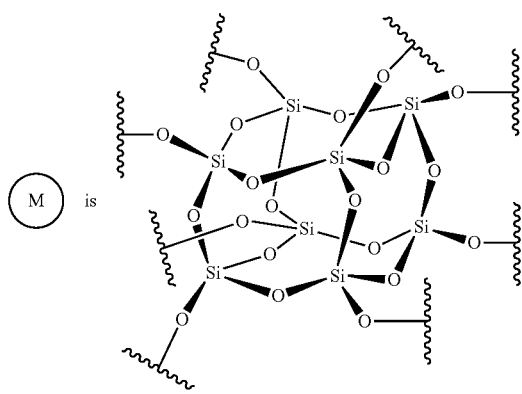
is a is 0 or 1, b is 0 or 1, c is 0 or 1, with the proviso that at least a or b is 1, and that if b is 1, then c is also 1, $R^1$ and $R^2$ are independently from each other $C_{1-4}$-alkyl, $R^3$, $R^4$, $R^5$ and $R^6$ are independently from each other hydrogen or $C_{1-4}$-alkyl, $R^7$, $R^8$ and $R^9$ are of formula (2), wherein $L^4$ is $C_{1-20}$-alkylene, phenylene-$C_{1-20}$-alkylene or $C_{1-20}$-alkylene-phenylene-$C_{1-20}$-alkylene, $R^{11}$, $R^{12}$, $R^{13}$ and $R^{14}$ are independently from each other hydrogen or $C_{1-4}$-alkyl, $R^{15}$, $R^{16}$, $R^{17}$ and $R^{18}$ are independently from each other $C_{1-4}$-alkyl, $R^{19}$ is $C_{1-20}$-alkyl, which may be substituted with phenyl, O—$C_{1-6}$-alkyl or $NO_2$, d is an integer from 1 to 25, or $R^7$, $R^8$ and $R^9$ are independently from each other $C_{1-20}$-alkyl, which may be substituted with one or more substituents selected from the group consisting of $C_{6-14}$-aryl, $OC_{1-6}$-alkyl and $NO_2$, with the proviso that at least one of $R^7$, $R^8$ and $R^9$ is of formula (2), or $R^7$ is of formula (2) and $R^8$ and $R^9$ together with the N linked to both of them form a 5, 6 or 7 membered ring, which may also include O or S, $L^1$ is -$L^{1a}$-$[X^{1a}]_o$-$[L^{1b}]_p$-, $L^2$ is -$[L^{2a}]_q$-$[X^{2a}]_r$—, $L^3$ is —$[X^{3a}]_s$-$[L^{3a}$-$X^{3b}]_t$-$[L^{3b}]_u$-, wherein o, p, q, r, s, t and u are independently from each other 0 or 1, $L^{1a}$, $L^{1b}$, $L^{2a}$, $L^{3a}$ and $L^{3b}$ are independently of each other $C_{1-20}$-alkylene, $C_{1-20}$-alkylene-phenylene, $C_{1-20}$-alkylene-$C_{5-8}$-cycloalkylene, phenylene or $C_{5-8}$-cycloalkylene, wherein $L^{1a}$, $L^{1b}$, $L^{2a}$, $L^{3a}$ and $L^{3b}$ may be substituted with one or more substituents selected from the group consisting of halogen, $OC_{1-6}$-alkyl, $NO_2$ and OH, or $L^{1b}$ and $R^7$ or $L^{2a}$ and $R^7$ together with the N linked to both of them form a 5, 6 or 7 membered ring, or $L^{3b}$ and $R^8$ together with the N linked to both of them form a 5, 6 or 7 membered ring, and $X^{1a}$, $X^{2a}$, $X^{3a}$ and $X^{3b}$ are independently of each other O, S, C(O) or C(O)O, and D is the chromophoric moiety, which may be substituted with one or more substituents selected from the group consisting of $C_{1-10}$-alkyl, phenyl, halogen, $OC_{116}$-alkyl, OH, $NH_2$ and $NO_2$.

Preferred are compounds of formula (3) wherein $R^6$ and $R^{12}$ are hydrogen.

In particular preferred compounds of formula (3) are

3A

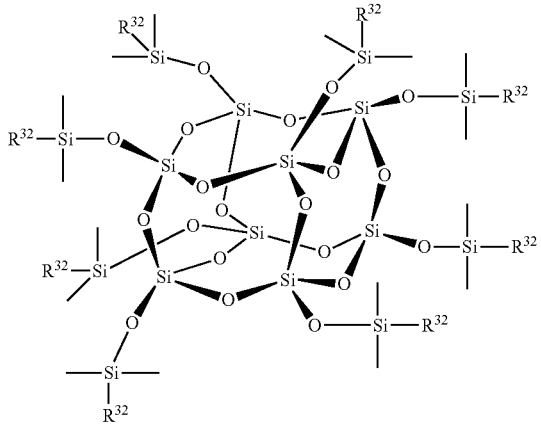

wherein $R^{32}$ is

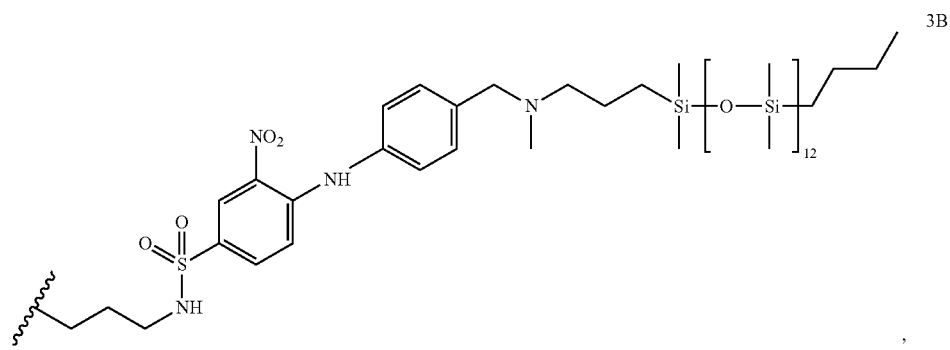
3B
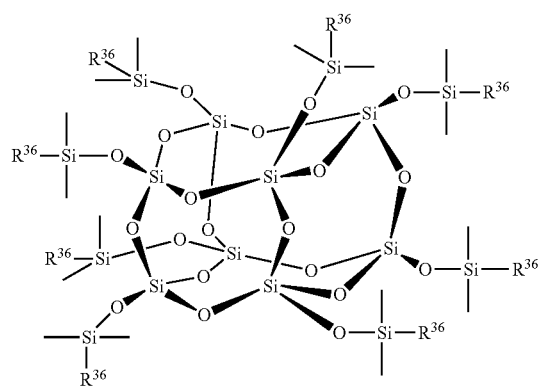
wherein
R³⁶ is
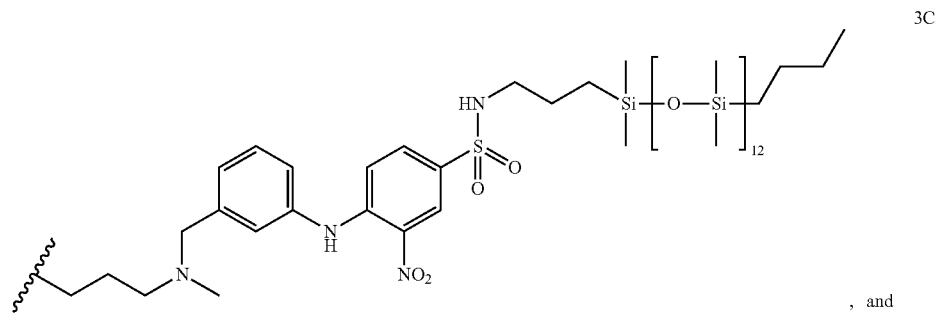
3C
, and
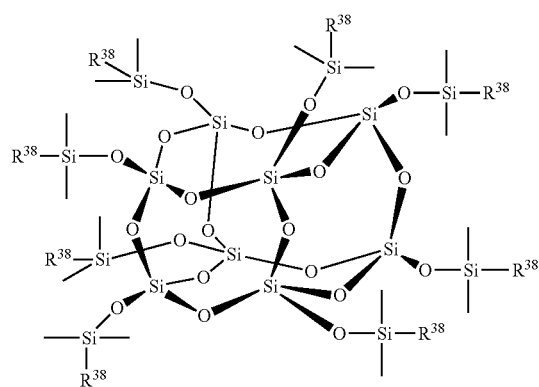
wherein
R³⁸ is

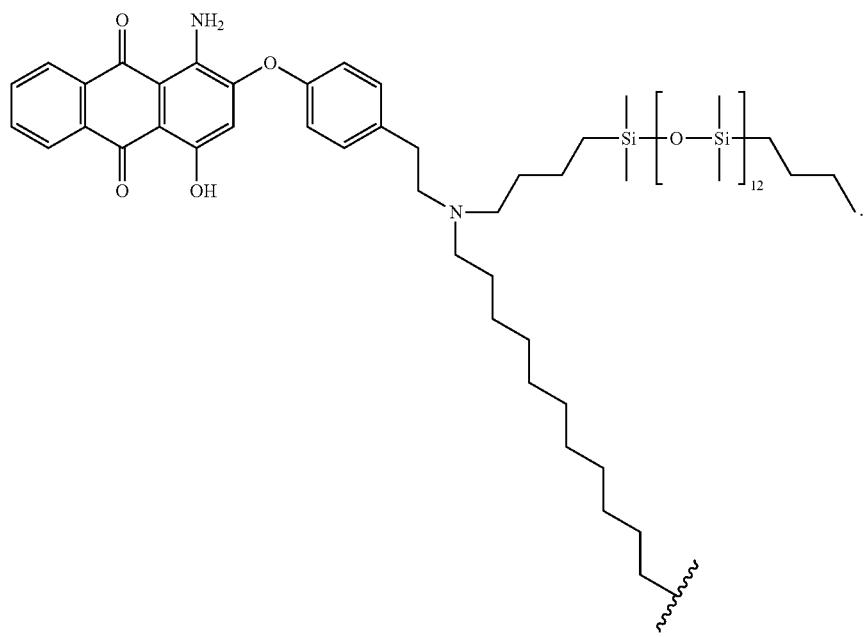

The compounds of formula (3) are soluble in apolar organic solvents. For example the compound of formula 3A is highly soluble in hexane and diethyl ether. For example, the compounds of formulae 3B and 3C are highly soluble in hexane.

The salts of the present invention usually have an average particle size of from 0.5 to 1.5 nm, preferably of from 0.8 to 1.2 nm.

The salts of the present invention are colored. The color of the salts of the present invention depends on the chromophoric moiety D.

For example, if the chromophoric moiety D is of formula

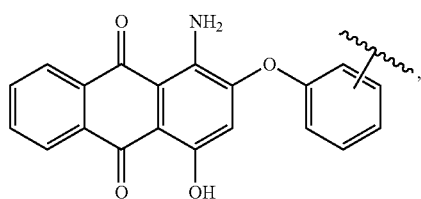

the salts of the present invention are magenta.

For example, if the chromophoric moiety $D^1$ is of formulae

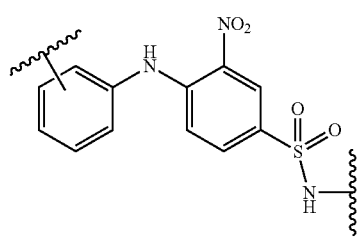

the salts of the present invention are yellow.

The salts of the present invention can be used in as colored particles in electrophoretic devices, preferably in electrophoretic displays, more preferably in electronic paper.

Also part of the present invention is an electrophoretic device comprising the salts of the present invention. Preferably, the electrophoretic device is an electrophoretic display, more preferably electronic paper. The electronic device can be flexible.

The electrophoretic device comprising a salt of the present invention can be prepared by a process comprising the steps of (i) forming a dispersion of the salt of the present invention in a dielectric fluid, and (ii) placing the dispersion obtained in step (i) between a pair of electrodes.

The dielectric fluid is preferably dodecane or a silicon oil having a viscosity which suits this application. The dispersion obtained in step (i) can contain further additives known to a person skilled in the art. The dispersion obtained in step (i) can be encapsulated in microcapsules or incorporated in foils containing microcavities by methods known to a person skilled in the art before being placed between the pair of electrodes in step (ii).

The salts of the present invention are charged colored particles suitable for use in full-colour electronic paper.

The salts of the present invention have an average particle size of 0.5 to 1.5 nm, preferably 0.8 to 2 nm, and show a narrow size distribution. Thus, the charged coloured particles of the present invention are suitable for use in video applications based on CMY technology. In addition the salts of the present invention do not show multiple pictures known as "ghosting" phenomena in electrophoretic devices. The salt of the present invention form homogeneous and stable dispersions or even solutions in dielectric fluids such as dodecane or silicon oil. For example, the compound of formula 1A gives a transparent solution in various silicon oils.

The process for the preparation of the salt of the present invention is advantageous, as the process allows the targeted preparation of the charged colored particles, consisting of defined supra-molecular structures, in particular with regard to the number of charges of the cation. A further advantage of the process is that the last step can be performed, and is preferably performed, under water-free conditions in an apolar organic solvent due to the good solubility of the compounds of formula (3) in apolar organic solvents yielding salts of the present invention that are not contaminated with traces of water. The lower the water-content of the salts of the present invention the better is their long-term performance in electrophoretic devices.

EXAMPLES

Example 1

Preparation of Compound 7A

'Karstedt-catalyst' solution (sold by Fluka, 2% (w/v) in iso-propanol, 0.75 ml) is diluted with dichloromethane (100 ml) and stirred at room temperature for 15 min under argon. Compound 11A (4.6 g), dissolved in dichloromethane (130 ml), and compound 10A (2.00 g) are added to the catalyst solution. The reaction mixture is heated to 40° C. A 1 molar solution of diethyl sulfide in dichloromethane (0.25 ml) is injected into the reaction mixture under vigorous stirring of the reaction mixture and stirring is continued until consumption of compound 11A as confirmed by $^1$H-NMR. After evaporation of approximately half of the solvent, the reaction mixture is purified by column chromatography (silica gel; eluent: dichloromethane to dichloromethane/methane 1:1) to yield compound 7A (3.3 g).

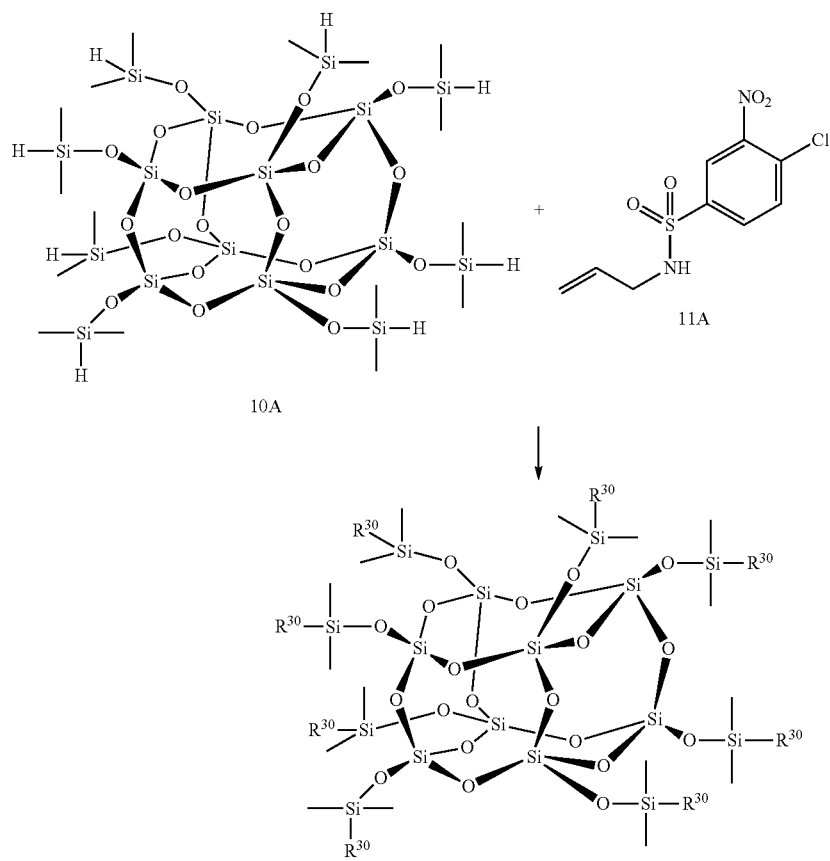

wherein
$R^{30}$ is $^1$H-NMR (CDCl$_3$, 300 MHz): δ=0.88 (6 H); 0.67 (2 H); 1.52 (2 H); 2.98 (2 H); 5.54 (NH); 7.31 (d, 1 H); 7.99 (dd, 1 H); 8.35 (d, 1 H). $^{29}$Si-NMR (CDCl$_3$, 80 MHz): δ=−110; +14.

Example 2

Preparation of Compound 9A

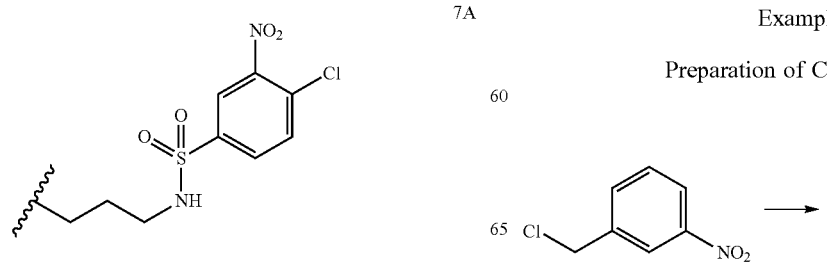

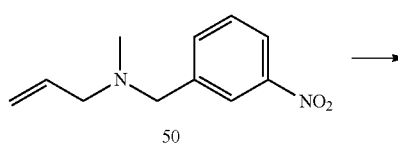

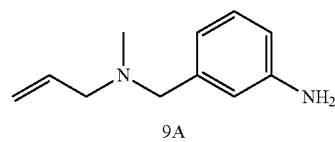

Preparation of Compound 50

A suspension of N-allylmethyl amine (12.2 g), 3-nitrobenzyl chloride (28.3 g) and sodium carbonate (17.5 g) in chloroform (350 ml) is vigorously stirred at 65° C. until consumption of 3-nitrobenzyl chloride. The reaction mixture is cooled, filtered and evaporated. The resulting residue is subsequently filtered over silica gel (eluent: dichloromethane) to give compound 50 (31.1 g), which is used without further purification.

$^1$H-NMR (CDCl$_3$, 300 MHz): δ=2.18 (s, 3 H); 3.03 (dd, 2 H); 3.56 (s, 2 H); 5.21 (ddd, 2 H); 5.89 (ddd, 1 H); 7.45 (t, 1 H); 7.64 (d, 1 H); 8.07 (ddd, 1 H); 8.17 (d, 1 H). $^{13}$C-NMR (CDCl$_3$, 75 MHz): δ=42.0; 60.5; 117.8; 122.0; 123.5; 129.1; 134.9; 135.4; 141.7; 148.3.

Preparation of Compound 9a

A mixture of compound 50 (31.0 g), tin granules (28.5 g) and dioxane (250 ml) is treated with concentrated hydrogen chloride (50 ml). The reaction mixture is filtered, diluted with ethyl acetate and the pH is adjusted to 9 with 2 N sodium hydroxide solution. After extraction, compound 9A (26.4 g) is obtained.

$^1$H-NMR (CDCl$_3$, 300 MHz): δ=2.03 (s, 3 H); 3.03 (dd, 2 H); 3.40 (s, 2 H); 4.12 (2 HN); 5.17 (ddd, 2 H); 5.92 (ddd, 1 H); 6.53 (ddd, 1 H); 6.64 (s, 1 H); 6.69 (s, 1 H); 7.05 (t, 1 H) $^{13}$C-NMR (CDCl$_3$, 75 MHz): δ=42.1; 60.6; 60.8; 113.9; 115.7; 117.6; 119.4; 129.1; 135.9; 140.2; 146.5.

Example 3

Preparation of Compound 5A

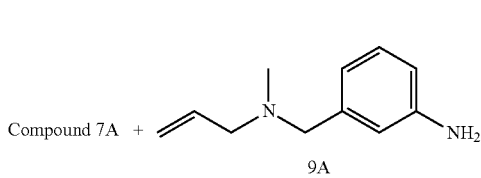

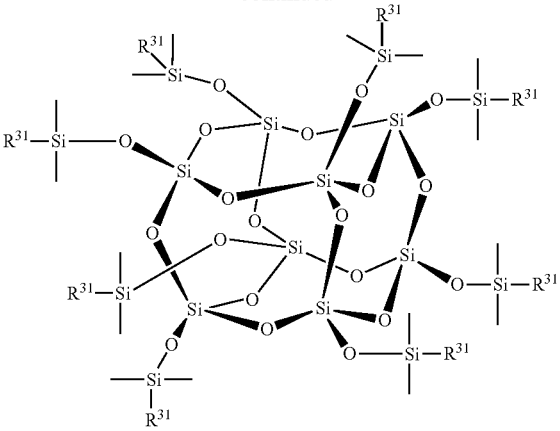

wherein
R$^{31}$ is

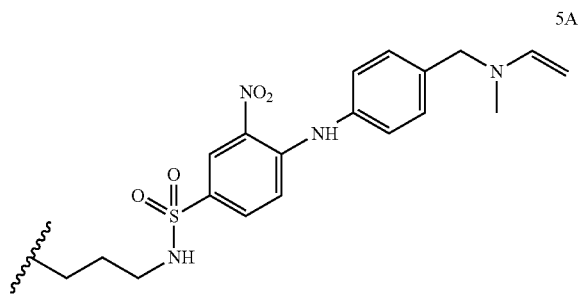 [SMILES: *CCCNS(=O)(=O)c1ccc(Nc2ccc(CN(C)C=C)cc2)c([N+](=O)[O-])c1]

A solution of compound 7A (2.0 g), compound 9A (0.97 g) and di-isopropyl ethyl amine (2.2 g) in dimethyl sulfoxide (10 ml) is heated to 100 C for 50 h. After cooling the reaction mixture, diethyl ether is poured into the reaction mixture and the precipitate is removed by filtration. The precipitate is dissolved in a mixture of dichloromethane and methanol and again precipitated. This precipitation-procedure is repeated several times. The precipitate is dissolved in a mixture of dichloromethane and a minimum methanol and the solution is washed with saturated sodium hydrogen carbonate. Evaporation of the solvent yields compound 5A (1.7 g).

$^1$H-NMR (CDCl$_3$, 300 MHz): all signals broad δ=0.07 (6 H); 0.51 (2 H); 1.58 (2 H); 2.21 (3 H); 2.95 (2 H); 3.05 (2 H); 3.47 (2 H); 5.56 (2 , H); 5.88 (ddd, 1 H); 7.25 (6 H); 7.76 (1 H); 8.68 (1 H); 9.79 (NH). $^{29}$Si-NMR (CDCl$_3$, 80 MHz): δ=−110; +14.

Example 4

Preparation of Compound 3A

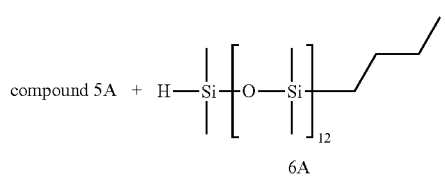

-continued

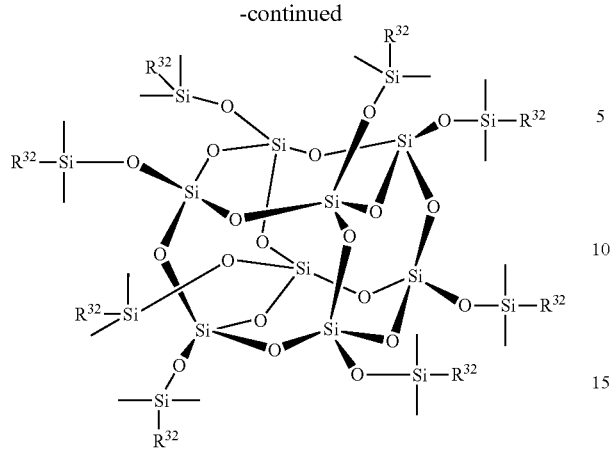

wherein
R$^{32}$ is

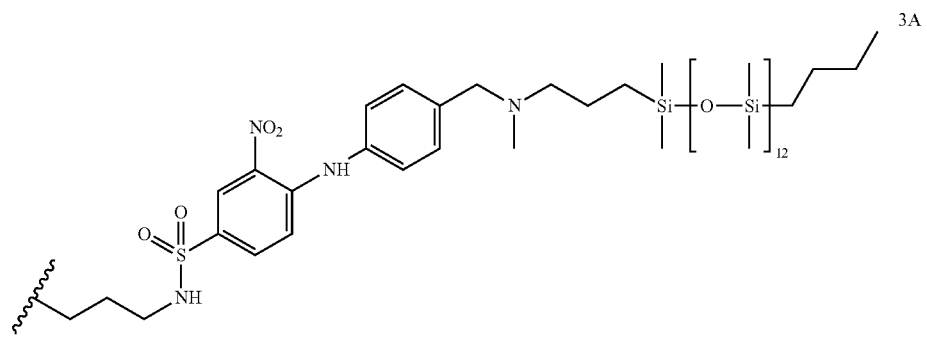

'Karstedt-catalyst' solution (sold by Fluka, 2% (w/v) in iso-propanol, 0.03 ml) is added to a mixture of compound 5A (79 mg), commercial compound 6A (polydimethylsiloxane, monohydride terminated sold by ABCR, 141 mg) and dichloromethane (2 ml) under argon. The reaction mixture is heated to 40° C. A 1 molar solution of diethyl sulfide in dichloromethane (0.01 ml) is injected into the reaction mixture under vigorous stirring and stirring is continued until consumption of compound 5A as confirmed by $^{1}$H-NMR. The reaction mixture is poured into hexane at room temperature and traces of catalyst are removed via filtration. The filtrate is evaporated to yield compound 3A (200 mg).

$^{1}$H-NMR (CDCl$_{3}$, 300 MHz): all signals broad δ=0.12 (84 H); 0.57 (6 H); 1.24 (t, 3 H); 1.32 (8 H); 1.61 (2 H, NH); 2.21 (3 H); 2.94 (4 H); 3.94 (2, H); 7.21 (5 H); 7.79 (2 H); 8.66 (2 H); 9.76 (NH).

Example 5

Preparation of Compound 1A compound 3A + 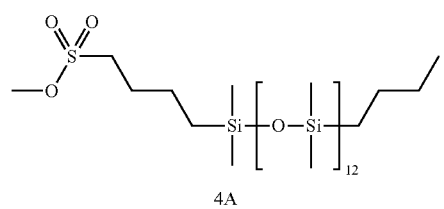

4A

↓

-continued

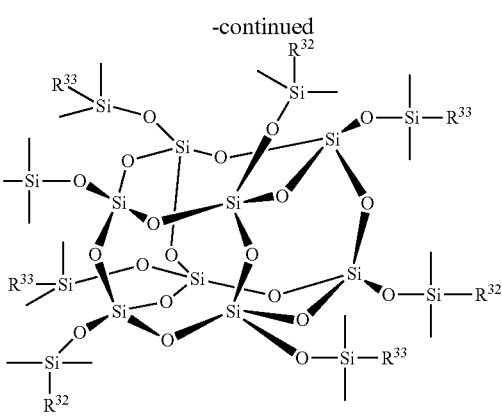

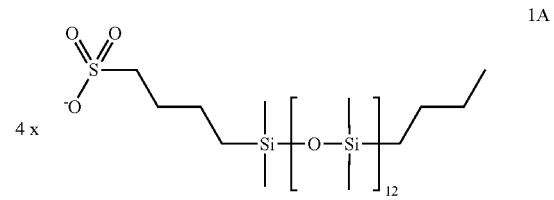

1A wherein
R$^{32}$ is and
R$^{33}$ is
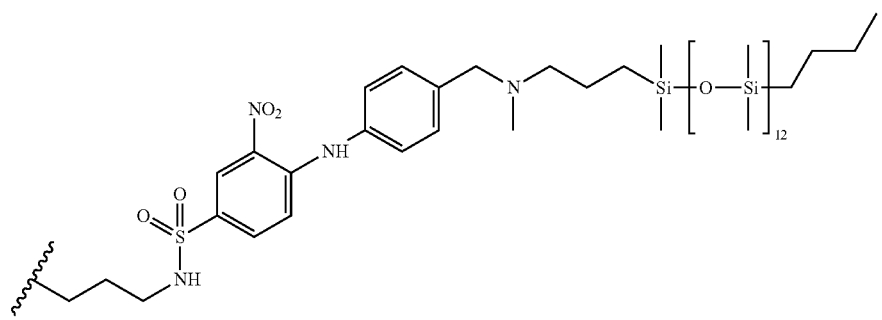
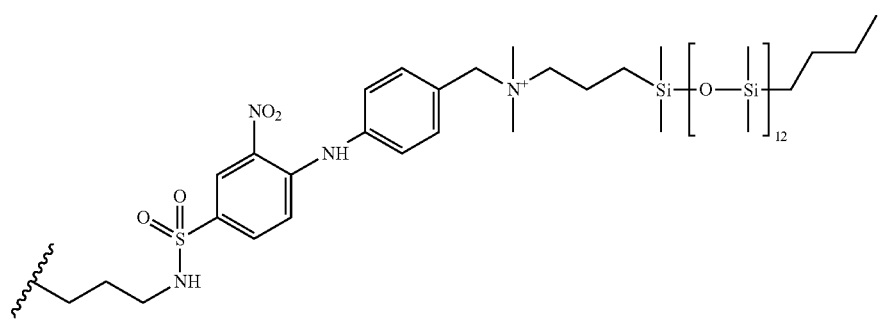
A mixture of compound 3A (148 mg), 4 equivalents of compound 4A and chloroform (3 ml) is heated to reflux until the methyl sulfonate signal of compound 4A disappears in the $^1$H-NMR spectrum. Compound 1A is obtained after evaporation the solvent (200 mg, 98%).
Example 6
Preparation of Compound 8A
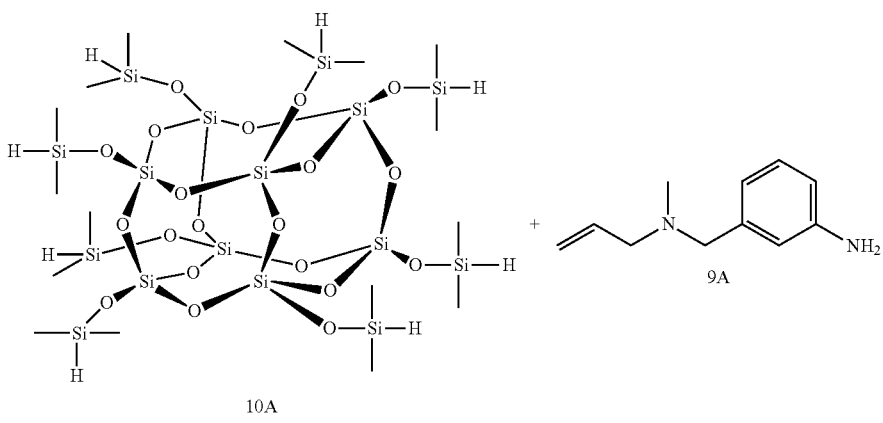

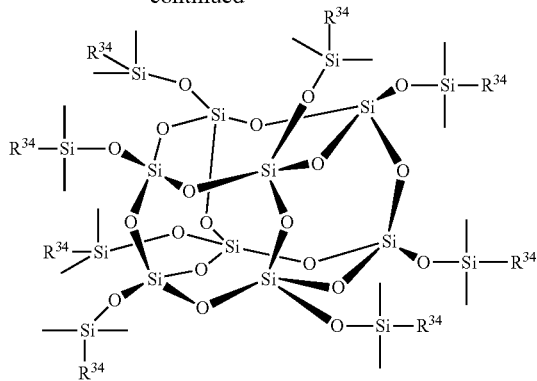

wherein R³⁴ is

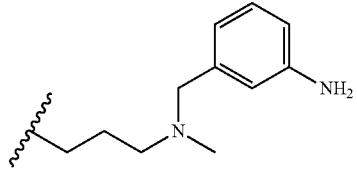

8A

'Karstedt-catalyst' solution (sold by Fluka, 2% (w/v) in iso-propanol, 0.06 ml) is added to a mixture of compound 10A (100 mg), compound 9A (150 mg) and dichloromethane (8 ml) under argon. The reaction mixture is heated to 40° C. A 1 molar solution of diethyl sulfide in dichloromethane (0.02 ml) is injected into the reaction mixture under vigorous stirring and stirring is continued until consumption of compound 9A as confirmed by ¹H-NMR. The reaction mixture is cooled to room temperature and poured into hexane. The precipitate is dissolved in dichloromethane and precipitated again by addition of hexane. After a second precipitation, the precipitate is dried to yield compound 8A (130 mg).

¹H-NMR (CDCl₃, 300 MHz): all signals broad δ=0.16 (48 H); 0.61 (16 H); 1.58 (16 H); 2.20 (24 H); 2.39 (16 H); 3.43 (16 H); 3.80 (16 NH); 6.67 (8 H); 6.69 (16 H); 7.09 (8 H). ¹³C-NMR (CDCl₃, 75 MHz): δ=0.2; 15.2; 20.3; 42.0; 60.8; 62.4; 113.6; 115.7; 119.4; 129.1; 140.1; 146.5. ²⁹Si-NMR (CDCl₃, 80 MHz): δ=−110; +14.

Example 7

Preparation of Compound 5B

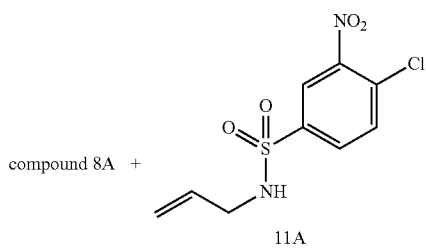

compound 8A +

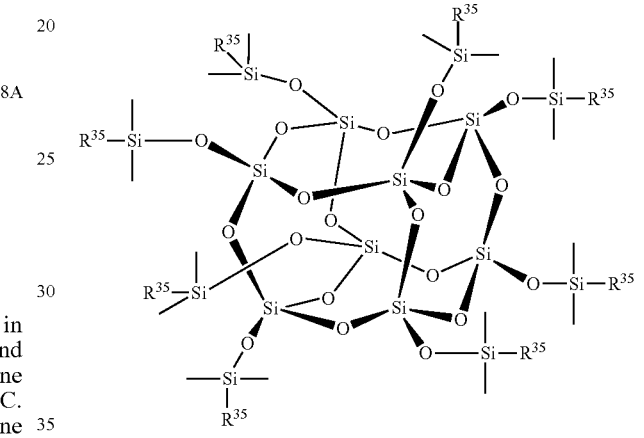

wherein R³⁵ is

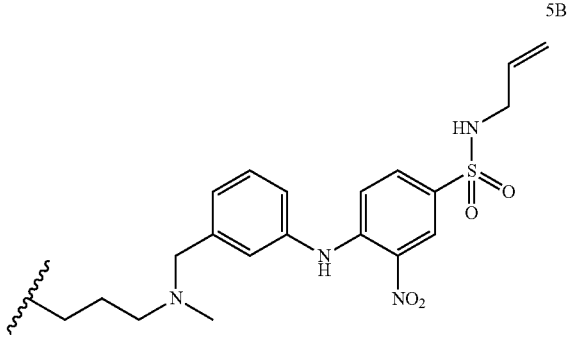 [SMILES: *CCCN(C)Cc1cccc(Nc2ccc(S(=O)(=O)NCC=C)cc2[N+](=O)[O-])c1]

5B

A solution of compound 8A (1.00 g), compound 11A (0.96 g), di-isopropyl ethylamine (1.5 ml) and dimethyl sulfoxide (5 ml) are heated at 100° C. for 50 h. The reaction mixture is cooled to room temperature and poured into diethyl ether to precipitate compound 5B. Compound 5B is redissolved in a mixture of dichloromethane and methanol and precipitated a second time. A solution of compound 56 in a mixture of dichloromethane and methanol is subsequently washed with saturated sodium hydrogen carbonate solution, dried over sodium sulfate and evaporated to give compound 5B (0.9 g).

¹H-NMR (CDCl₃, 300 MHz): all signals broad δ=0.12 (48 H); 0.57 (16 H); 1.55 (16 H); 2.16 (24 H); 2.39 (16 H); 3.49

(16 H); 3.61 (16 H); 5.17 (16 H); 5.75 (8 H); 7.23 (40 H); 7.38 (8 H); 7.74 (8 H); 8.72 (8 H); 9.80 (8 NH). $^2$Si-NMR (CDCl$_3$, 80 MHz): δ=−110; +14.

Example 8

Preparation of Compound 3B

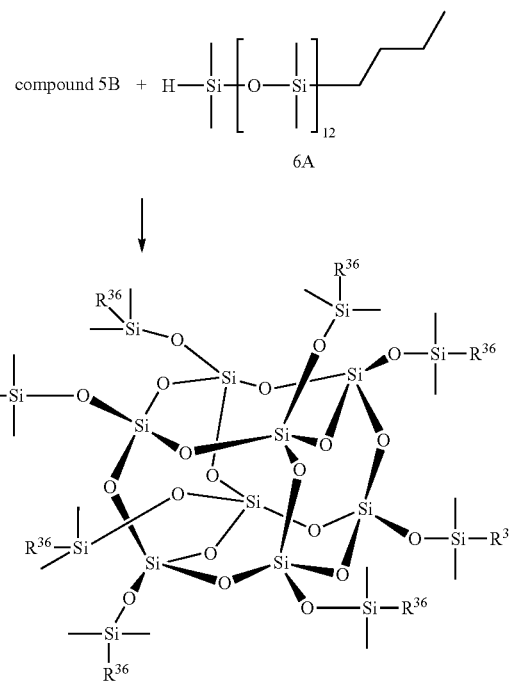

wherein R$^{36}$ is

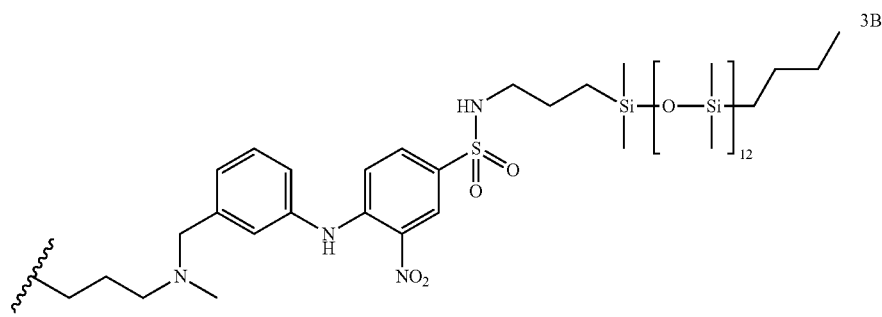

'Karstedt-catalyst' solution (sold by Fluka, 2% (w/v) in iso-propanol, 0.2 ml) is added to a mixture of compound 5B (0.95 g), compound 6A (polydimethylsiloxane, monohydride terminated sold by ABCR, 1.7 g) and dichloromethane (10 ml) under argon. The reaction mixture is heated to 40° C. A 1 molar solution of diethyl sulfide in dichloromethane (0.08 ml) is injected into the reaction mixture under vigorous stirring and stirring is continued for 48 h. The reaction mixture is copied to room temperature and evaporated to dryness. The residue is taken up in hexane and traces of catalyst are removed via filtration. The filtrate is evaporated to yield compound 3B (2.83 g, 98%).

$^1$H-NMR (CDCl$_3$, 300 MHz): all signals broad δ=0.07 (ca. 126 H); 0.59 (32H); 0.89 (24 H); 1.29 (16 H); 1.59 (32 H); 2.17 (24 H); 2.35 (16 H); 2.97 (16 H); 3.51 (16 H); 7.25 (40 H); 7.39 (8 H); 7.77 (8 H); 8.71 (8 H); 9.79 (8 NH).

Example 9

Preparation of Compound 1B

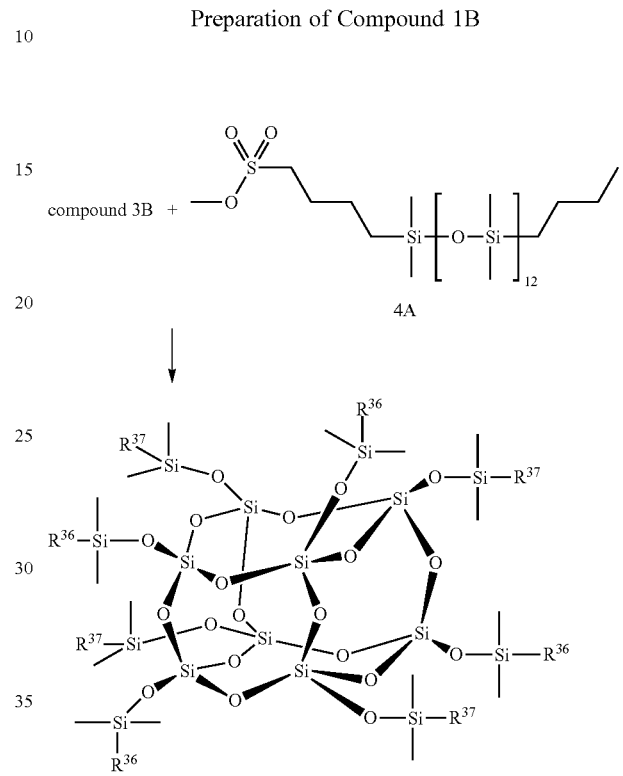

-continued

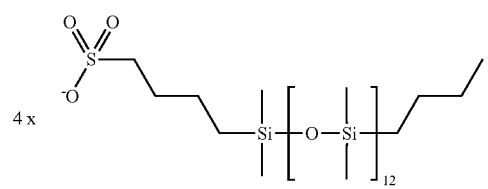

wherein R$^{36}$ is wherein  
R$^{37}$ is
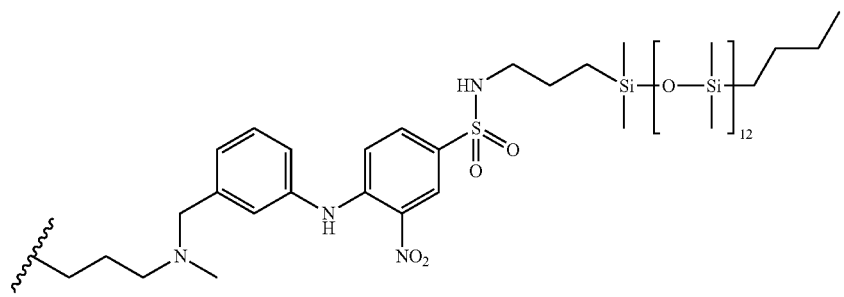
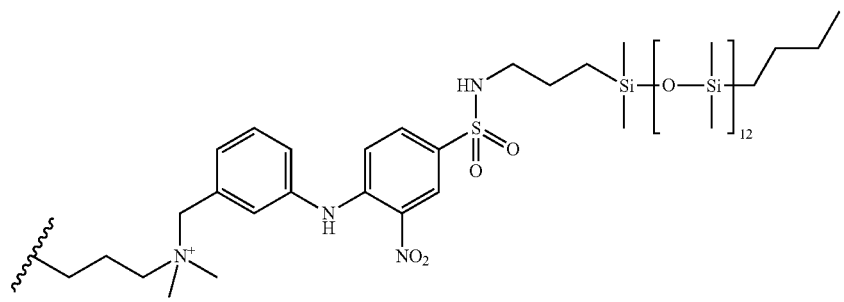
A mixture of compound 3B (200 mg), 4 mole equivalents of compound 4A (73 mg) and chloroform (4 ml) is heated to reflux for 75 h. Compound 1B (273 mg, 100%) is obtained after evaporation the solvent.
Example 10
Preparation of Compound 1C
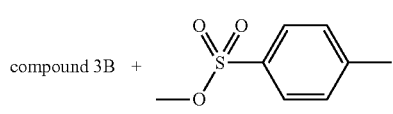
-continued
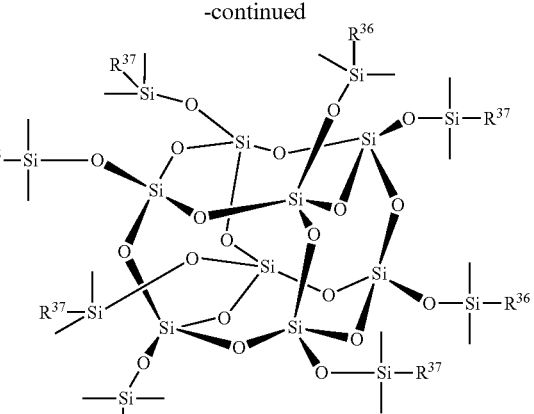
wherein  
R$^{36}$ is
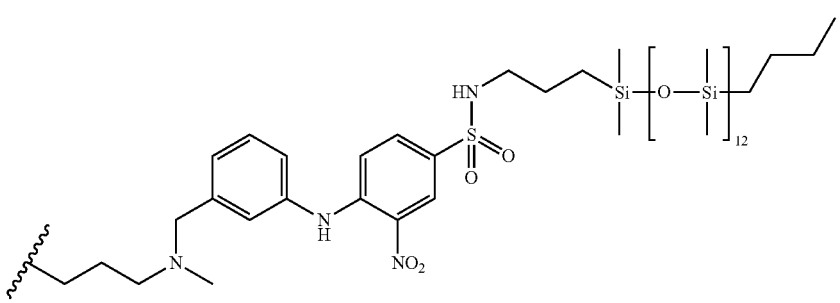

and
R³⁷ is

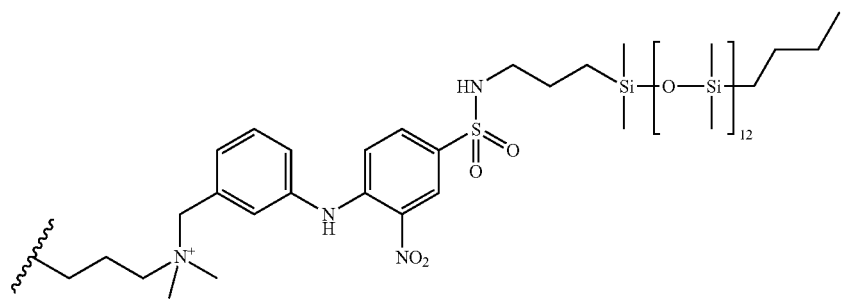

A mixture of compound 3B (200 mg), 4 mole equivalents of compound 4B (16 mg) and chloroform (4 ml) is heated to reflux for 24 h. Compound 1C is obtained after evaporation the solvent in quantitative yield.

Example 11

Preparation of Compound 4C

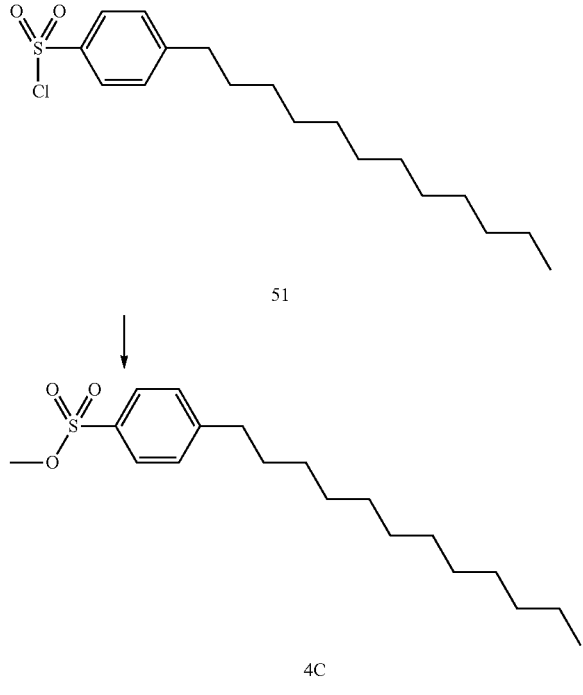

Preparation of Compound 51

4-Dodecylbenzene sulfonic acid (mixture of isomers sold by Fluka) (50 g) is reacted with phosphoxy chloride (22 ml) at 120 C for four hours. Excess phosphoxy chloride is distilled off at 58 mbar. The residue is dissolved at 0 C in dichloromethane and extracted with ice-water. Evaporation of the solvent yields compound 51 (51.3 g).

Preparation of compound 4C

Compound 51 (10 g) is dissolved in methanol (40 mL) at 0° C. and is treated with 2 M sodium methoxide solution (20 ml). The reaction mixture is slowly warmed to room temperature. After 24 h the reaction mixture is filtered to yield a syrupy mass, which is purified via passage over a silica gel pad (eluent: dichloromethane) to yield compound 4C (4.1 g).
¹H-NMR (CDCl₃, 300 MHz): all signals broad δ=3.77 (s, 3 H); 7.30 (m, 2 H); 7.88 (m, 2 H). ¹³C-NMR (CDCl₃, 75 MHz): δ=56.1.

Example 12

Preparation of Compound 1D

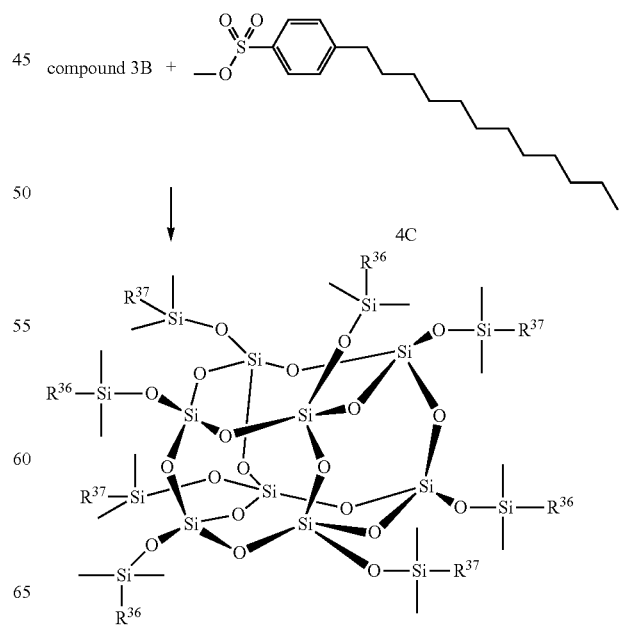

wherein R$^{36}$ is

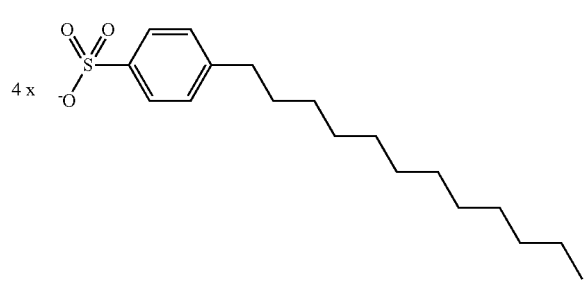

and R$^{37}$ is

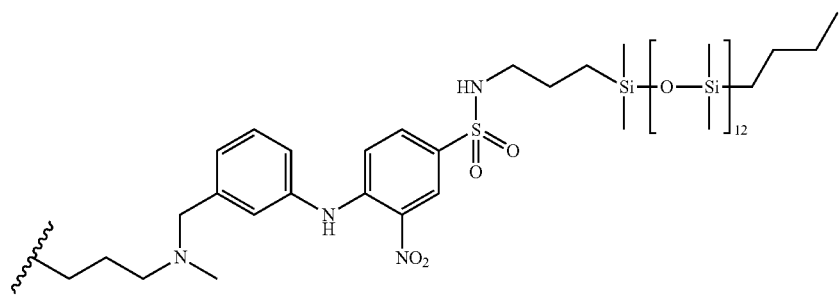

A mixture of compound 3B (200 mg), 4 mole equivalents of compound 4C (23 mg) and chloroform (4 ml) is heated to reflux until methyl transfer is completed according to $^1$H-NMR inspection. Compound 1D (223 mg, 100%) is obtained after evaporation the solvent.

Example 13

Preparation of Compound 12A

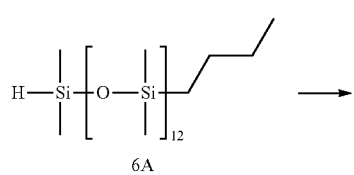

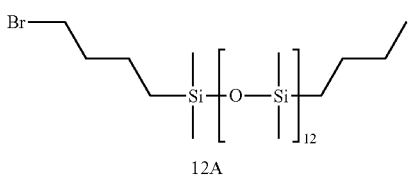

Compound 6A (polydimethylsiloxane, monohydride terminated sold by ABCR, 50.0 g) and 4-bromo-butene (7.25 g) are dissolved in toluene (100 ml) under argon and heated to 60 C. The reaction mixture is treated with 1.5 ml of a 'Speier-catalyst-solution' (0.1 g H$_2$PtCl$_6$ in 10 ml iso-propanol) for 48 hours. Removal of solvent and filtration of the colorless residue over silica gel (eluent dichloromethane) gives compound 12A (47.7 g).

$^1$H-NMR (CDCl$_3$, 300 MHz): δ=0.14 (ca. 78 H); 0.57 (4 H); 0.95 (t, 3 H); 1.28 (6 H); 1.48 (2 H); 1.92 (2 H); 3.34 (2 H). $^{13}$C-NMR (CDCl$_3$, 75 MHz): δ=0.1; 1.0; 13.7; 17.2; 17.9; 21.1; 24.1; 33.4; 35.2.

Example 13

Preparation of Compound 13A

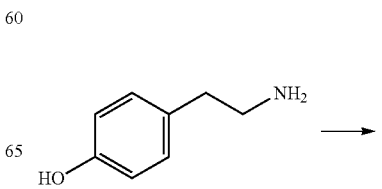

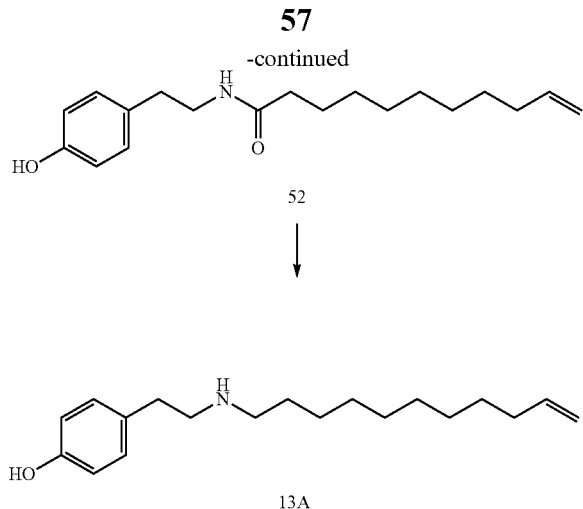

Preparation of Compound 52

Tyramine (sold by Aldrich, 16 g) and di-iso-propyl ethylamine (42 ml) are dissolved at 0° C. in dimethylformamide (300 ml). Undecenyl acid chloride (30.1 g) is added dropwise under vigorous stirring. The reaction mixture is slowly warmed to room temperature. Stirring is continued for 24 hours. Evaporation of the solvent yields compound 52 (36.4 g).

$^1$H-NMR (CDCl$_3$, 300 MHz): δ=1.25 (10 H); 1.34 (dt, 2 H); 1.59 (t, 2 H); 2.02 (dd, 2 H); 2.15 (dd, 2 H); 2.56 (t, 2 H); 4.96 (ddd, 1 H); 5.81 (m, 2 H); 6.81 (d, 2 H); 6.99 (d, 2 H). $^{13}$C-NMR (CDCl$_3$, 75 MHz): δ=27.8; 29.1; 29.2; 29.3; 29.4; 33.7; 34.7; 36.7; 41.0; 114.2; 115.7; 121.5; 129.5; 139.4; 155.6; 174.6.

Preparation of Compound 13A

Compound 52 is dissolved in dry tetrahydrofuran (140 ml) and dropped to a slurry of lithium aluminium hydride (5.1 g) in tetrahydrofuran (300 ml) under argon. The reaction mixture is refluxed for 30 h. The reaction mixture is subsequently cooled to 0° C. and cautiously poured into ice-water and filtered over Celite. The aqueous phase is then extracted with ethyl acetate. The organic phase is washed with brine, dried over sodium sulfate, filtered and evaporated to dryness to yield compound 13A as an oil, which is purified by column chromatography (silica gel; eluent: dichloromethane/methanol 20:1) to yield compound 13A (14.1 g).

$^1$H-NMR (CDCl$_3$, 300 MHz): δ=1.26 (12 H); 1.36 (t, 2 H); 1.52 (t, 2 H); 2.06 (dt, 2 H); 2.67 (t, 2 H); 2.78 (t, 2 H); 2.90 (t, 2 H); 4.99 (ddd, 1 H); 5.53 (broad NH, OH); 5.83 (m, 1 H); 6.75 (d, 2 H); 7.01 (d, 2 H). $^{13}$C-NMR (CDCl$_3$, 75 MHz): δ=27.3; 28.9; 29.2; 29.4; 29.4; 33.0; 34.5; 49.4; 50.1; 50.4; 114.1; 116.0; 129.7; 129.8; 139.2; 155.9.

Example 14

Preparation of Compound 14A

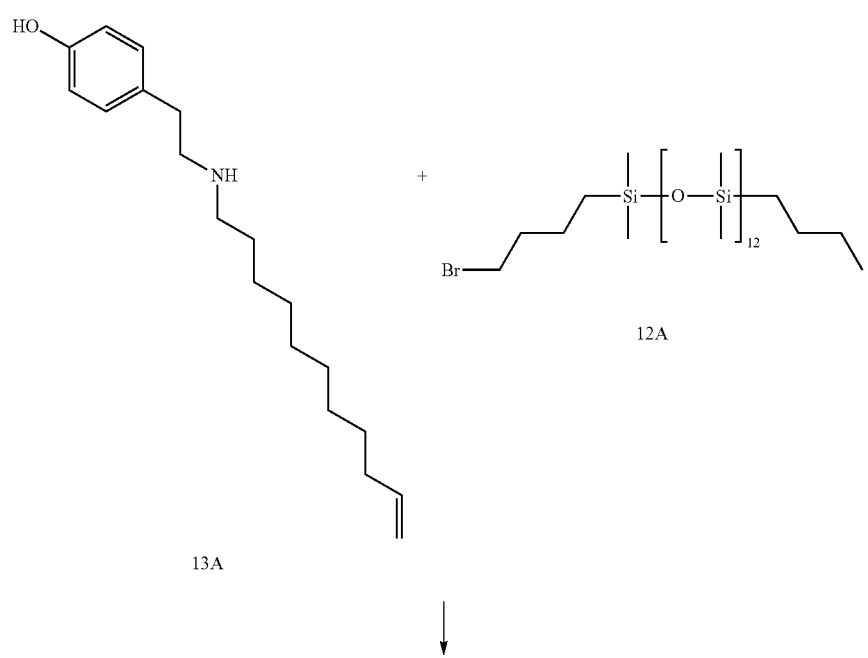

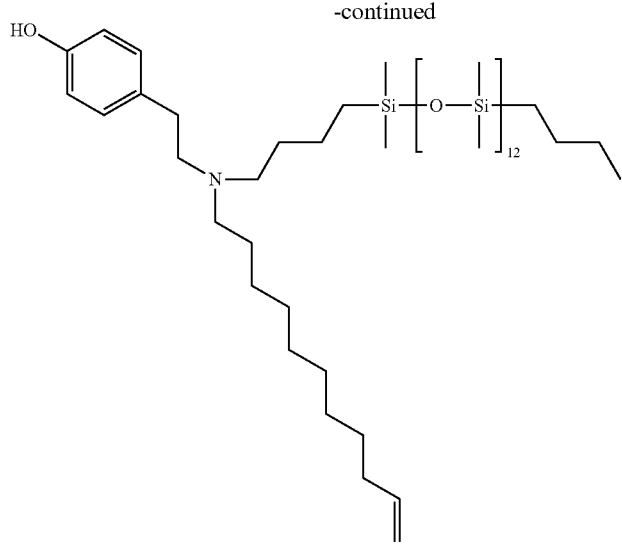

14A

Compound 13A (2.7 g) and compound 12A (10.0 g) are dissolved in a mixture of acetonitrile (12 ml) and dioxane (25 ml) containing potassium iodide (1 g). After addition of potassium carbonate (1.2 g) the suspension is heated to 80° C. under argon for 24 hours. After cooling to room temperature the reaction mixture is filtered over Celite and purified by column chromatography (silica gel; eluent: dichloromethane/methanol 25:1) to yield compound 14A (4.9 g).

$^1$H-NMR (CDCl$_3$, 300 MHz): δ=0.11 (78 H); 0.58 (dt, 4 H); 0.91 (t, 3 H); 1.30 (14 H); 1.59 (4 H); 2.05 (dt, 2 H); 2.66 (4 H); 2.79 (4 H); 4.99 (ddd, 2 H); 5.84 (ddd, 1 H); 6.77 (d, 2 H); 7.01 (d, 2 H). $^{13}$C-NMR (CDCl$_3$, 75 MHz): δ=0.1; 1.1; 11.1; 17.9; 18.0; 21.1; 25.4; 26.3; 27.2; 28.9; 28.8; 29.1; 29.4; 33.7; 52.9; 53.1; 54.9; 114.2; 115.9; 129.7; 129.8; 139.1; 155.7.

Example 15

Preparation of Compound 16A

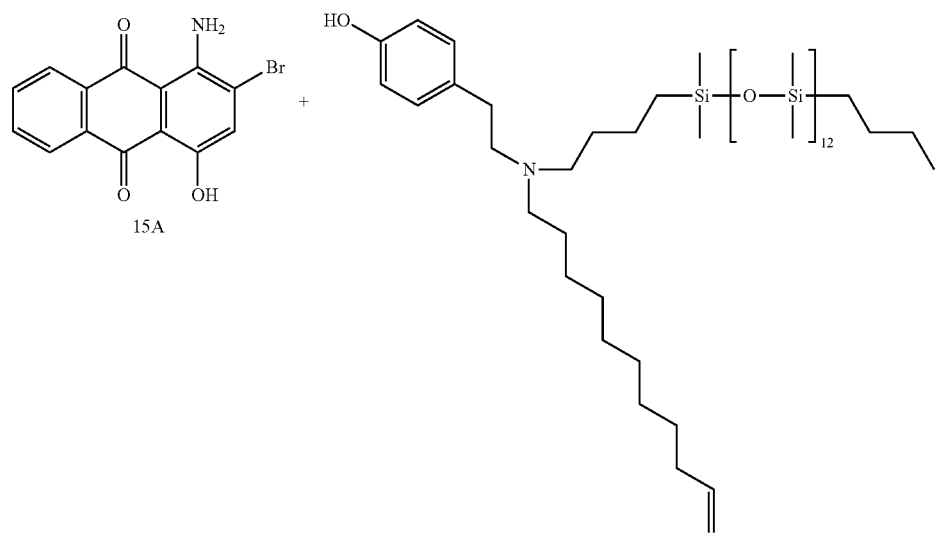

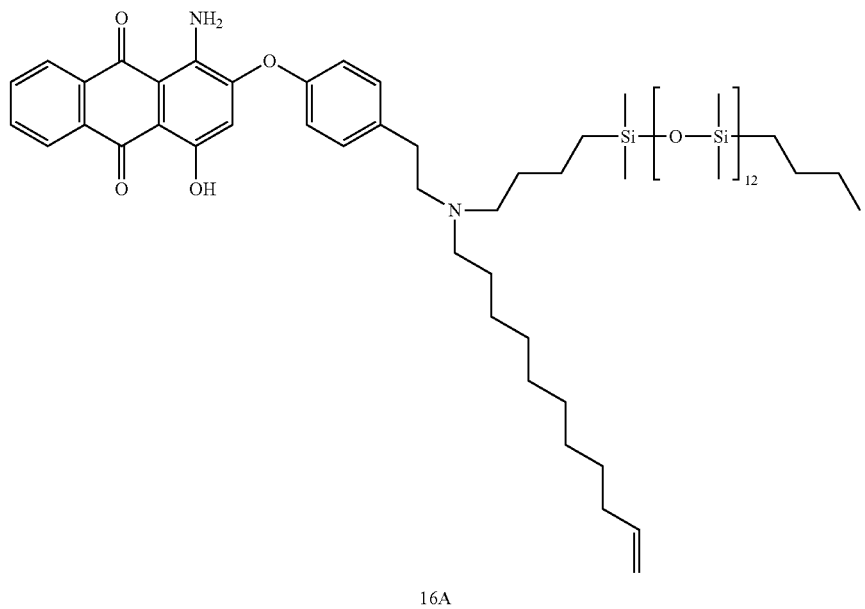

16A

1-Amino-2-bromo-4-hydroxy anthrachinone (275 mg) and 1.0 g of compound 14A (1.0 g) are dissolved in chloroform (20 ml) containing cesium carbonate (0.51 g) and the reaction mixture is refluxed for 48 hours. Addition of dimethylformamide (1 ml) improves the solubility during progress of the reaction. The reaction mixture is cooled to room temperature, diluted with ethyl acetate and extracted with brine and water. Evaporation of the solvent gives a residue, which is purified by column chromatography (silica gel; eluent: hexane/ethyl acetate 10:2) to yield compound 16A 1781 (0.133 g).

$^1$H-NMR (CDCl$_3$, 300 MHz): δ=0.11 (78 H); 0.58 (dt, 4 H); 0.92 (t, 3 H); 1.32 (18 H); 1.47 (4 H); 2.05 (dt, 2 H); 2.53 (dt, 4 H); 2.73 (2 H); 2.80 (2 H); 4.99 (ddd, 2 H); 5.84 (ddd, 1 H); 6.41 (s. 1 H); 7.01 (d, 2 H); 7.28 (d, 2 H); 7.78 (dt, 2 H); 8.36 (dd, 2H). $^{13}$C-NMR (CDCl$_3$, 75 MHz): δ0.1; 1.1; 13.8; 14.1; 18.1; 18.4; 21.3; 22.1; 26.3; 27.2; 28.9; 29.2; 29.4; 29.6; 29.7; 33.7; 33.8; 53.9; 54.2; 56.2; 108.7; 109.4; 114.1; 120.9; 126.3; 126.8; 130.6; 132.9; 133.4; 133.6; 135.0; 139.1; 139.2; 150.5; 155.5; 159.6; 183.2; 185.5.

Example 16

Preparation of Compound 3C

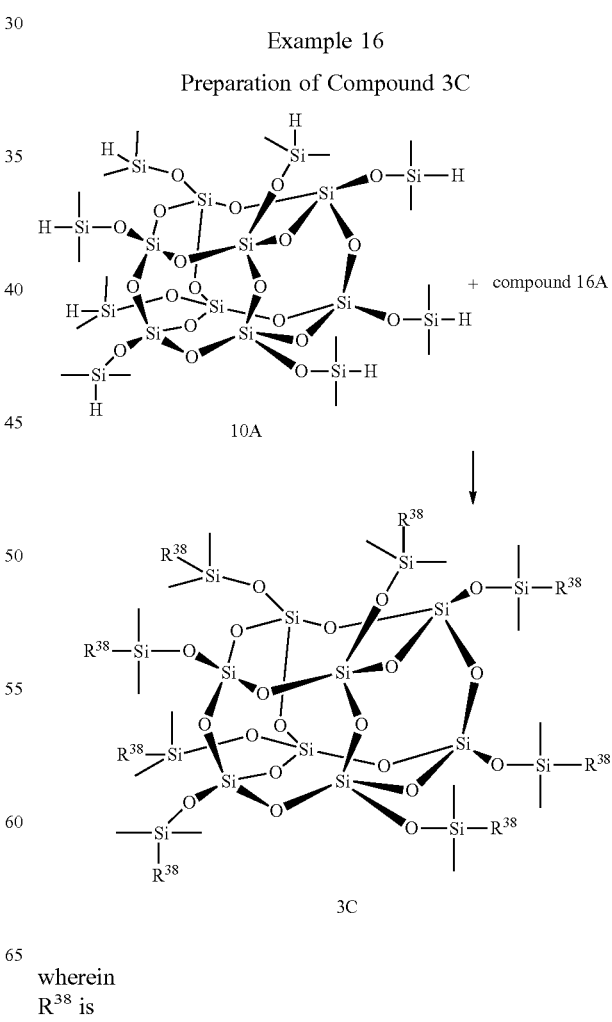

wherein R$^{38}$ is

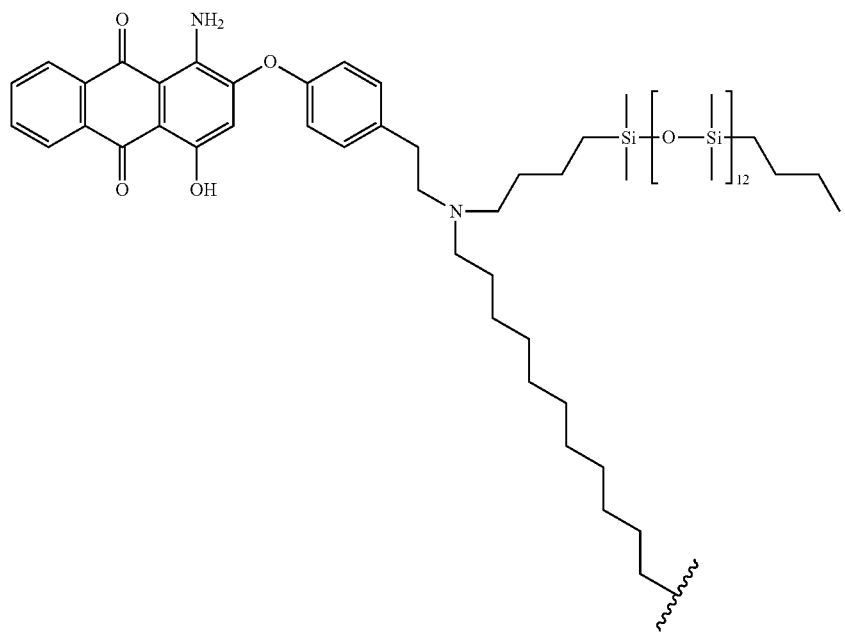

Compound 16A (133 mg) is reacted with compound 10A (10 mg) in dry toluene (5 ml) in the presence of 'Karstedt-catalyst-solution (sold by Fluka, 2% (w/v) in iso-propanol, 0.01 ml) under argon at 45° C. After 3 days the reaction mixture is cooled and purified by column chromatography (silica gel; eluent: heptane/ethyl acetate 10:1) to yield compound 3C (80 mg).

$^1$H-NMR (CDCl$_3$, 300 MHz): all signals broad δ=0.11 (78 H); 0.58 (dt, 6 H); 0.92 (3 H); 1.32 (20 H); 1.72 (4 H); 1.95 (4 H); 2.93 (2 H); 3.08 (2 H); 3.23 (2 H); 3.40 (1 H); 6.61 (s, 1 H); 7.11 (2 H); 7.38 (2 H); 7.75 (2 H); 8.30 (dd, 2 H).

The invention claimed is:

1. A salt of a cation and an anion, wherein the cation comprises
   (i) a silsesquioxane moiety of formula

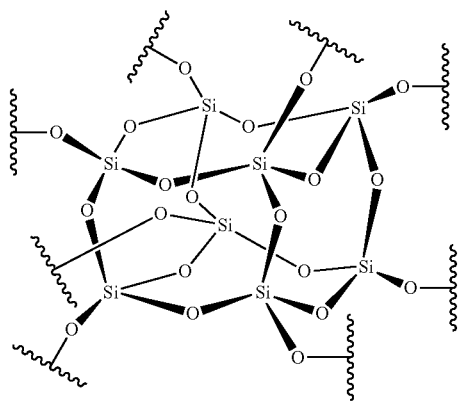 [SMILES: *O[Si]12O[Si]3(O*)O[Si@]4(O*)O[Si@](O*)(O1)O[Si@@]1(O*)O[Si@@](O*)(O2)O[Si@](O*)(O3)O[Si@@](O*)(O4)O1]

(ii) a chromophoric moiety D, which may which may be substituted with one or more substituents selected from the group consisting of $C_{1-10}$-alkyl, phenyl, halogen, $OC_{1-6}$-alkyl, OH, $NH_2$ and $NO_2$, and
   (iii) a moiety of formula

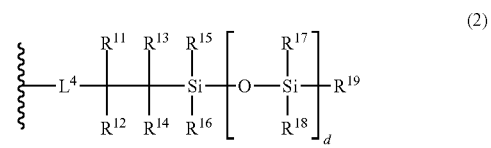

(2)

wherein $L^4$ is $C_{1-20}$-alkylene, phenylene-$C_{1-20}$-alkylene or $C_{1-20}$-alkylene-phenylene-$C_{1-20}$-alkylene, $R^{11}$, $R^{12}$, $R^{13}$ and $R^{14}$ are independently from each other hydrogen or $C_{1-4}$-alkyl, $R^{15}$, $R^{16}$, $R^{17}$ and $R^{18}$ are independently from each other $C_{1-4}$-alkyl, $R^{19}$ is $C_{1-20}$-alkyl, which may be substituted with phenyl, O—$C_{1-6}$-alkyl or $NO_2$, and d is an integer from 1 to 25.

2. The salt of claim 1, wherein $L^4$ is $C_{1-20}$-alkylene, phenylene-$C_{1-20}$-alkylene or $C_{1-20}$-alkylene-phenylene-$C_{1-20}$-alkylene, $R^{12}$ is hydrogen, $R^{11}$, $R^{13}$ and $R^{14}$ are independently from each other hydrogen or $C_{1-4}$-alkyl, $R^{15}$, $R^{16}$, $R^{17}$ and $R^{18}$ are independently from each other $C_{1-4}$-alkyl, $R^{19}$ is $C_{1-20}$-alkyl, which may be substituted with phenyl, O—$C_{1-6}$-alkyl or $NO_2$, and d is an integer from 1 to 25.

3. The salt of claim 1, wherein $L^4$ is $C_{1-10}$-alkylene, $R^{11}$, $R^{12}$, $R^{13}$ and $R^{14}$ are hydrogen, $R^{15}$, $R^{16}$, $R^{17}$ and $R^{18}$ are methyl, $R^{19}$ is $C_{1-10}$-alkyl, and d is an integer from 8 to 16.

4. The salt of claim 1, wherein the salt is of formula

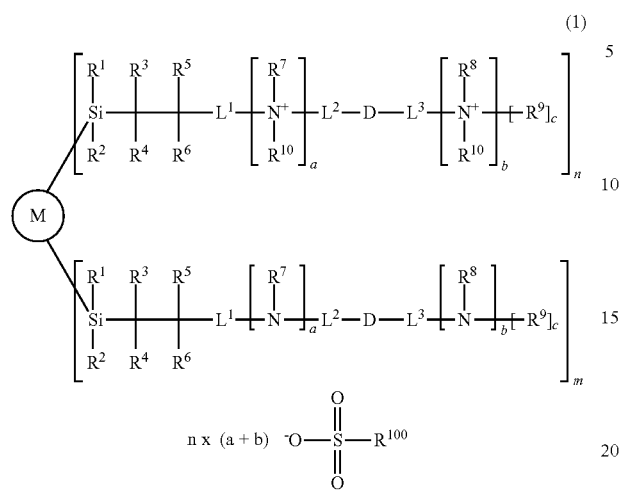

(1)

wherein

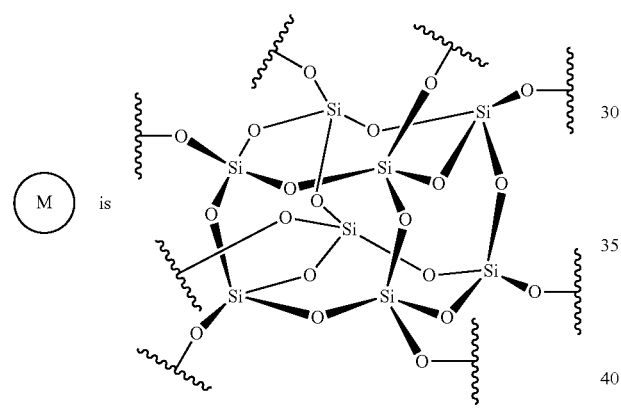

M is n is 1, 2, 3, 4, 5, 6, 7 or 8,
m is 8-n,
a is 0 or 1,
b is 0 or 1,
c is 0 or 1,
with the proviso that at least a or b is 1, and that if b is 1, then c is also 1,
$R^1$ and $R^2$ are independently from each other $C_{1-4}$-alkyl,
$R^3$, $R^4$, $R^5$ and $R^6$ are independently from each other hydrogen or $C_{1-4}$-alkyl,
$R^7$, $R^8$ and $R^9$ are independently from each other of formula (2) or $C_{1-20}$-alkyl, which $C_{1-20}$-alkyl may be substituted with one or more substituents selected from the group consisting of $C_{6-14}$-aryl, $OC_{1-6}$-alkyl and $NO_2$, with the proviso that at least one of $R^7$, $R^8$ and $R^9$ is of formula (2), or
$R^7$ is of formula (2) and $R^8$ and $R^9$ together with the N linked to both of them form a 5, 6 or 7 membered ring, which may also include O or S,
$R^{10}$ is $C_{1-20}$-alkyl, which may be substituted with one or more substituents selected from the group consisting of $C_{6-14}$-aryl, $OC_{1-6}$-alkyl and $NO_2$,
$L^1$ is $-L^{1a}-[X^{1a}]_o-[L^{1b}]_p-$,
$L^2$ is $-[L^{2a}]_q-[X^{2a}]_r-$,
$L^3$ is $-[X^{3a}]_s-[L^{3a}-X^{3b}]_t-[L^{3b}]_u-$,
wherein
o, p, q, r, s, t and u are independently from each other 0 or 1,
$L^{1a}$, $L^{1b}$, $L^{2a}$, $L^{3a}$ and $L^{3b}$ are independently of each other $C_{1-20}$-alkylene, $C_{1-20}$-alkylene-phenylene, $C_{1-20}$-alkylene-$C_{5-8}$-cycloalkylene, phenylene or $C_{5-8}$-cycloalkylene, wherein $L^{1a}$, $L^{1b}$, $L^{2a}$, $L^{3a}$ and $L^{3b}$ may be substituted with one or more substituents selected from the group consisting of halogen, $OC_{1-6}$-alkyl, $NO_2$ and OH, or
$L^{1b}$ and $R^7$ or $L^{2a}$ and $R^7$ together with the N linked to both of them form a 5, 6 or 7 membered ring, or
$L^{3b}$ and $R^8$ together with the N linked to both of them form a 5, 6 or 7 membered ring, and
$X^{1a}$, $X^{2a}$, $X^{3a}$ and $X^{3b}$ are independently of each other O, S, C(O) or C(O)O, and
D is the chromophoric moiety, which may be substituted with one or more substituents selected from the group consisting of $C_{1-10}$-alkyl, phenyl, halogen, $OC_{1-6}$-alkyl, OH, $NH_2$ and $NO_2$, and
$R^{100}$ is

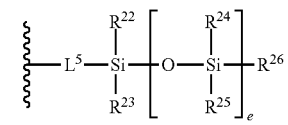

wherein
$L^5$ is $C_{1-20}$-alkylene,
$R^{22}$, $R^{23}$, $R^{24}$ and $R^{25}$ are independently from each other $C_{1-4}$-alkyl,
$R^{26}$ is $C_{1-20}$-alkyl, which may be substituted with phenyl, $O-C_{1-6}$-alkyl or $NO_2$, and
e is an integer from 1 to 25, or
$R^{100}$ is $-C_{1-20}$-alkylene-Y$-[-[CH_2]_x-Y-]_y-C_{1-10}$-alkyl
wherein
Y is O or S,
x is an integer from 1 to 6, and
y is an integer from 1 to 25, or
$R^{100}$ is $C_{6-14}$-aryl, which may be substituted with $C_{1-20}$-alkyl, $OC_{1-6}$-alkyl or $NO_2$.

5. The salt of claim 4, wherein
$R^6$ is hydrogen and
$R^{10}$ is methyl.

6. The salt of claim 4, wherein
n is 1, 2, 3, 4, 5, 6, 7 or 8,
m is 8-n,
a is 0 or 1,
b is 0 or 1,
c is 0 or 1,
with the proviso that at least a or b is 1, and that if b is 1, then c is also 1,
$R^1$ and $R^2$ are independently from each other $C_{1-4}$-alkyl,
$R^3$, $R^4$ and $R^5$ are independently from each other hydrogen or $C_{1-4}$-alkyl,
$R^6$ is hydrogen,
$R^7$, $R^8$ and $R^9$ are independently from each other of formula (2) or $C_{1-20}$-alkyl, which $C_{1-20}$-alkyl may be substituted with one or more substituents selected from the group consisting of $C_{6-14}$-aryl, $OC_{1-6}$-alkyl and $NO_2$, with the proviso that at least one of $R^7$, $R^8$ and $R^9$ is of formula (2),
$R^{10}$ is methyl, L1 is -L1a-[X1a]o-[L1b]p-,
L² is -[L²ᵃ]_q-[X²ᵃ]_r-,
L³ is —[X³ᵃ]_s-[L³ᵃ-X³ᵇ]_t-[L³ᵇ]_u-,
wherein
o, p, q, r, s, t and u are independently from each other 0 or 1,
$L^{1a}$, $L^{1b}$, $L^{2a}$, $L^{3a}$ and $L^{3b}$ are independently of each other $C_{1-20}$-alkylene, $C_{1-20}$-alkylene-phenylene, $C_{1-20}$-alkylene-$C_{5-8}$-cycloalkylene, phenylene or $C_{5-8}$-cycloalkylene, wherein $L^{1a}$, $L^{1b}$, $L^{2a}$, $L^{3a}$ and $L^{3b}$ may be substituted with one or more substituents selected from the group consisting of halogen, $OC_{1-6}$-alkyl, $NO_2$ and OH,
$X^{1a}$, $X^{2a}$, $X^{3a}$ and $X^{3b}$ are independently of each other O, S, C(O) or C(O)O, and
D is the chromophoric moiety, which may be substituted with one or more substituents selected from the group consisting of $C_{1-10}$-alkyl, phenyl, halogen, $OC_{1-6}$-alkyl, OH, $NH_2$ and $NO_2$.

7. The salt of claim 4, wherein
n is 1, 2, 3, 4, 5, 6, 7 or 8,
m is 8-n,
a is 0 or 1,
b is 0 or 1,
c is 0 or 1,
with the proviso that at least a or b is 1, and that if b is 1, then c is also 1,
$R^1$ and $R^2$ are methyl
$R^3$, $R^4$, $R^5$ and $R^6$ are hydrogen,
$R^7$, $R^8$ and $R^9$ are independently from each other of formula (2) or $C_{1-6}$-alkyl, with the proviso that at least one of $R^7$, $R^8$ and $R^9$ is of formula (2),
$R^{10}$ is methyl,
L¹ is -L¹ᵃ-[X¹ᵃ]_o-[L¹ᵇ]_p-,
L² is -[L²ᵃ]_q-[X²ᵃ]_r-,
L³ is —[X³ᵃ]_s-[L³ᵃ-X³ᵇ]_t-[L³ᵇ]_u-,
wherein
q and u are independently from each other 0 or 1,
o, p, r, s and t are 0,
$L^{1a}$, $L^{1b}$, $L^{2a}$, $L^{3a}$ and $L^{3b}$ are independently of each other $C_{1-20}$-alkylene,
$X^{1a}$, $X^{2a}$, $X^{3a}$ and $X^{3b}$ are independently of each other O, S, C(O) or C(O)O, and
D is the chromophoric moiety, which may be substituted with one or more substituents selected from the group consisting of $C_{1-10}$-alkyl, phenyl, halogen, $OC_{1-6}$-alkyl, OH, $NH_2$ and $NO_2$.

8. The salt of claim 1, wherein the chromophoric moiety D is selected from the group consisting of

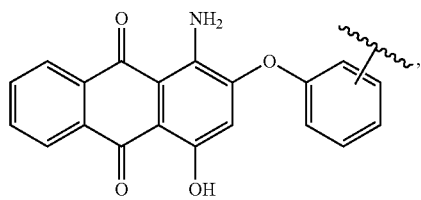

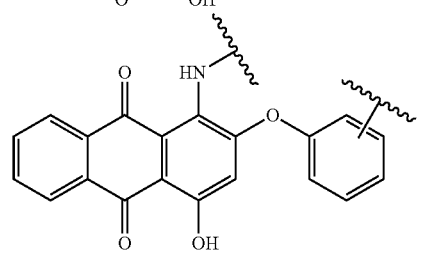

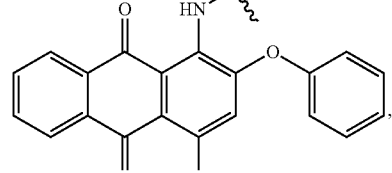

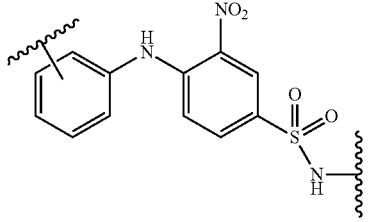

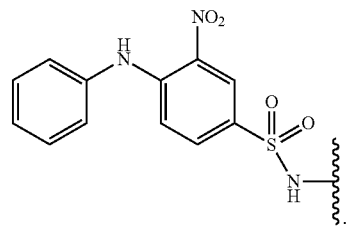
and

9. The salt of claim 4, wherein
$R^{100}$ is

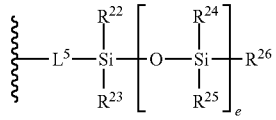

wherein
$L^5$ is $C_{1-20}$-alkylene,
$R^{22}$, $R^{23}$, $R^{24}$ and $R^{25}$ are independently from each other $C_{1-4}$-alkyl,
$R^{26}$ is $C_{1-20}$-alkyl, which may be substituted with phenyl, O—$C_{1-6}$-alkyl or $NO_2$, and
e is an integer from 1 to 25, or
$R^{100}$ is $C_{6-14}$-aryl, which may be substituted with $C_{1-20}$-alkyl, $OC_{1-6}$-alkyl or $NO_2$.

10. The salt of claim 4, wherein
$R^{100}$ is

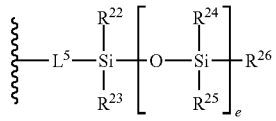

wherein
$L^5$ is $C_{1-6}$-alkylene,
$R^{22}$, $R^{23}$, $R^{24}$ and $R^{25}$ are independently from each other methyl,
$R^{26}$ is $C_{1-10}$-alkyl, and
e is an integer from 8 to 16, or
$R^{100}$ is phenyl, which is substituted with $C_{1-20}$-alkyl.

11. A process for the preparation of the salts of formula (1) of claim 4, which process comprises the step of reacting a compound of formula

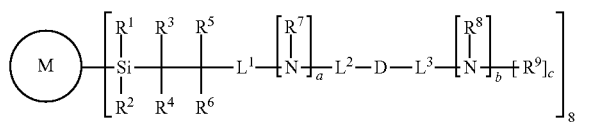 (3)

wherein
M, a, b, c, $R^1$, $R^2$, $R^3$, $R^4$, $R^5$, $R^6$, $R^7$, $R^8$, $R^9$, $L^1$, $L^2$, $L^3$ and D are as depicted in formula (1)
with a compound of formula

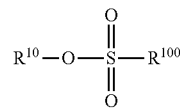 (4)

wherein
$R^{10}$ and $R^{100}$ are as depicted for formula (1).

12. An electrophoretic device comprising the salt of claim 1, wherein the salt is used as colored particles for the electrophoretic device.

13. The salt of claim 5, wherein
n is 1, 2, 3, 4, 5, 6, 7 or 8,
m is 8-n,
a is 0 or 1,
b is 0 or 1,
c is 0 or 1,
with the proviso that at least a or b is 1, and that if b is 1, then c is also 1,
$R^1$ and $R^2$ are independently from each other $C_{1-4}$-alkyl,
$R^3$, $R^4$ and $R^5$ are independently from each other hydrogen or $C_{1-4}$-alkyl,
$R^6$ is hydrogen,
$R^7$, $R^8$ and $R^9$ are independently from each other of formula (2) or $C_{1-20}$-alkyl, which $C_{1-20}$-alkyl may be substituted with one or more substituents selected from the group consisting of $C_{6-14}$-aryl, $OC_{1-6}$-alkyl and $NO_2$, with the proviso that at least one of $R^7$, $R^8$ and $R^9$ is of formula (2),
$R^{10}$ is methyl,
L1 is -L1a-[X1a]o-[L1b]p-,
$L^2$ is -$[L^{2a}]_q$-$[X^{2a}]_r$-,
$L^3$ is —$[X^{3a}]_s$-$[L^{3a}$-$X^{3b}]_t$-$[L^{3b}]_u$-,
wherein
o, p, q, r, s, t and u are independently from each other 0 or 1,
$L^{1a}$, $L^{1b}$, $L^{2a}$, $L^{3a}$ and $L^{3b}$ are independently of each other $C_{1-20}$-alkylene, $C_{1-20}$-alkylene-phenylene, $C_{1-20}$-alkylene-$C_{5-8}$-cycloalkylene, phenylene or $C_{5-8}$-cycloalkylene, wherein $L^{1a}$, $L^{1b}$, $L^{2a}$, $L^{3a}$ and $L^{3b}$ may be substituted with one or more substituents selected from the group consisting of halogen, $OC_{1-6}$-alkyl, $NO_2$ and OH,
$X^{1a}$, $X^{2a}$, $X^{3a}$ and $X^{3b}$ are independently of each other O, S, C(O) or C(O)O, and
D is the chromophoric moiety, which may be substituted with one or more substituents selected from the group consisting of $C_{1-10}$-alkyl, phenyl, halogen, $OC_{1-6}$-alkyl, OH, $NH_2$ and $NO_2$.

14. The salt of claim 4, wherein n is 8.

* * * * *